(12) United States Patent
Kang et al.

(10) Patent No.: US 9,728,730 B2
(45) Date of Patent: Aug. 8, 2017

(54) COMPOUND FOR ORGANIC OPTOELECTRIC DEVICE AND COMPOSITION AND ORGANIC OPTOELECTRIC DEVICE AND DISPLAY DEVICE

(71) Applicant: SAMSUNG SDI CO., LTD., Yongin-si, Gyeonggi-do (KR)

(72) Inventors: Dong-Min Kang, Suwon-si (KR); Eun-Sun Yu, Suwon-si (KR); Dong-Kyu Ryu, Suwon-si (KR); Sang-Shin Lee, Suwon-si (KR); Han-Ill Lee, Suwon-si (KR); Yu-Na Jang, Suwon-si (KR); Soo-Young Jeong, Suwon-si (KR); Su-Jin Han, Suwon-si (KR); Jin-Seok Hong, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 245 days.

(21) Appl. No.: 14/602,974

(22) Filed: Jan. 22, 2015

(65) Prior Publication Data

US 2015/0303381 A1    Oct. 22, 2015

(30) Foreign Application Priority Data

Apr. 22, 2014  (KR) ........................ 10-2014-0048323

(51) Int. Cl.
  *H01L 51/00*   (2006.01)
  *C07D 471/14*  (2006.01)
  *H01L 51/50*   (2006.01)

(52) U.S. Cl.
  CPC ........ *H01L 51/0072* (2013.01); *C07D 471/14* (2013.01); *H01L 51/0067* (2013.01);
  (Continued)

(58) Field of Classification Search
  None
  See application file for complete search history.

(56) References Cited

U.S. PATENT DOCUMENTS

| 4,143,142 A | 3/1979 | Adhikary |
| 4,255,573 A | 3/1981 | Adhikary |
| 4,863,930 A | 9/1989 | Adhikary |

FOREIGN PATENT DOCUMENTS

| CN | 102070632 A | 5/2011 |
| JP | 2009-054809 A | 3/2009 |

(Continued)

OTHER PUBLICATIONS

Akkaoui et al. (Tetrahedron 2012, 68, p. 9131).*

(Continued)

*Primary Examiner* — J. L. Yang
(74) *Attorney, Agent, or Firm* — Lee & Morse, P.C.

(57) ABSTRACT

Provided are a compound, a composition, a light emitting material including the same, an organic optoelectric device and a display device including the organic optoelectric device, and the compound is represented by the following Chemical Formula I,

[Chemical Formula I]

(Continued)

in the Chemical Formula I, $X^1$ to $X^8$, L and $R^1$ to $R^5$ are the same as defined in the specification.

19 Claims, 2 Drawing Sheets

(52) U.S. Cl.
CPC ...... *H01L 51/0073* (2013.01); *H01L 51/0074* (2013.01); *H01L 51/5016* (2013.01); *H01L 2251/5384* (2013.01)

(56) References Cited

FOREIGN PATENT DOCUMENTS

| | | |
|---|---|---|
| KR | 1988-0007078 A | 8/1988 |
| KR | 10-2011-0116635 A | 10/2011 |
| KR | 10-2015-0075169 | 7/2015 |

OTHER PUBLICATIONS

Ahmed El Akkaoui, et al.; "Straightforward Bienaymé and copper catalyzed N-arylation sequence to access diverse 5H-pyrido[2'1:2,3]imidazo[4,5-b]indoles and analogues";Tetrahedron 68 (2012) 9131-9138.

\* cited by examiner

COMPOUND FOR ORGANIC OPTOELECTRIC DEVICE AND COMPOSITION AND ORGANIC OPTOELECTRIC DEVICE AND DISPLAY DEVICE

CROSS-REFERENCE TO RELATED APPLICATION

This application claims priority to and the benefit of Korean Patent Application No. 10-2014-0048323 filed in the Korean Intellectual Property Office on Apr. 22, 2014, the entire contents of which are incorporated herein by reference.

BACKGROUND OF THE INVENTION (a) Field of the Invention

A compound for an organic optoelectric device, a composition, an organic optoelectric device and a display device are disclosed.

(b) Description of the Related Art

An organic optoelectric device is a device that converts electrical energy into photoenergy, and vice versa.

An organic optoelectric device may be classified as follows in accordance with its driving principles. One is an electronic device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectric device include an organic photoelectric device, an organic light emitting diode, an organic solar cell, and an organic photo-conductor drum, and the like.

Among them, the organic light emitting diode (OLED) has recently drawn attention due to an increase in demand for flat panel displays. The organic light emitting diode converts electrical energy into light by applying current to an organic light emitting material, and has a structure in which an organic is interposed between an anode and a cathode. Herein, the organic layer may include an emission layer and optionally an auxiliary layer, and the auxiliary layer may include, for example at least one layer selected from a hole injection layer, a hole transport layer, an electron blocking layer, an electron transport layer, an electron injection layer, and a hole blocking layer that improve efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

A compound for an organic optoelectric device being capable of realizing an organic optoelectric device having characteristics such as high efficiency, a long life-span, and the like is provided.

A composition for an organic optoelectric device including the compound for an organic optoelectric device, an organic optoelectric device, and a display device including the organic optoelectric device are provided.

In one embodiment of the present invention, a compound for an organic optoelectric device represented by the following Chemical Formula I is provided.

[Chemical Formula I]

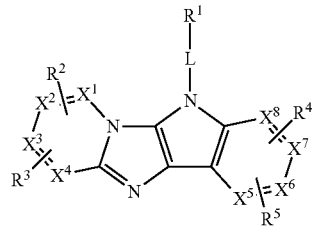

In the Chemical Formula I, $X^1$ to $X^8$ are independently N, C or $CR^a$,

L is a single bond, a substituted or unsubstituted C1 to C30 alkylene group, a substituted or unsubstituted C3 to C30 cycloalkylene group, a substituted or unsubstituted C3 to C30 heterocycloalkylene group, a substituted or unsubstituted C6 to C30 arylene group, or a substituted or unsubstituted C2 to C30 heteroarylene group, a substituted or unsubstituted C6 to C30 aryleneamine group, a substituted or unsubstituted C2 to C30 heteroaryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, $R^1$ is a substituted or unsubstituted C6 to C30 aryl group, a substituted or unsubstituted C2 to C30 heteroaryl group, or a combination thereof, $R^2$ to $R^5$ and $R^a$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C2 to C30 heteroarylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted C3 to C40 silyl group, a substituted or unsubstituted C3 to C40 silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C6 to C30 arylthiol group, a substituted or unsubstituted C1 to C30 heteroarylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof, and the $R^2$ and $R^3$, or $R^4$ and $R^5$ are independently present, or are fused to each other to provide a ring.

In another embodiment of the present invention, a composition for an organic optoelectric device including the compounds for an organic optoelectric device is provided.

In yet another embodiment of the present invention, an organic optoelectric device includes an anode and a cathode facing each other, and at least one organic layer interposed between the anode and the cathode, wherein the organic layer includes the compound for an organic optoelectric device or the composition for an organic optoelectric device.

In still another embodiment of the present invention, a display device including the organic optoelectric device is provided.

An organic optoelectric device having high efficiency and long life-span may be realized.

DETAILED DESCRIPTION

Figure 1:
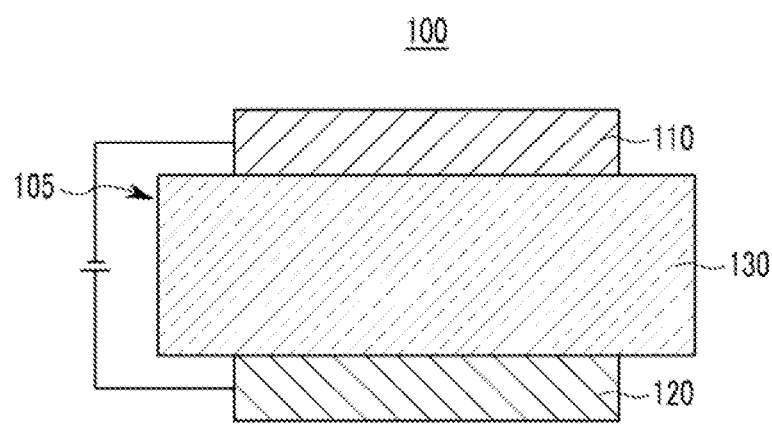
FIGS. 1 and 2 are cross-sectional views showing organic light emitting diodes according to embodiments.

Hereinafter, embodiments of the present invention are described in detail. However, these embodiments are exemplary, and this disclosure is not limited thereto.

As used herein, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like or a cyano group, instead of at least one hydrogen of a substituent or a compound.

The two adjacent substituent selected from the substituted halogen, hydroxy group, amino group, substituted or unsubstituted C1 to C20 amine group, a nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused to form a ring. Specifically, the substituted C6 to C30 aryl group may be fused to another adjacent substituted C6 to C30 aryl group to form a substituted or unsubstituted fluorene ring.

In the present specification, when specific definition is not otherwise provided, "hetero" refers to one including 1 to 3 hetero atoms selected from N, O, S, and P, and remaining carbons in one functional group.

In the present specification, when a definition is not otherwise provided, the term "combination thereof" refers to at least two substituents bound to each other by a linker, or at least two substituents condensed to each other.

In the present specification, when a definition is not otherwise provided, "alkyl group" refers to an aliphatic hydrocarbon group. The alkyl group may be 7 "a saturated alkyl group" without any double bond or triple bond.

The alkyl group may be a C1 to C20 alkyl group. More specifically, the alkyl group may be a C1 to C10 alkyl group or a C1 to C6 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, the term "aryl group" refers to a substituent including all element of the cycle having p-orbitals which form conjugation, and may be monocyclic, polycyclic or fused ring polycyclic (i.e., rings sharing adjacent pairs of carbon atoms) functional group.

As used herein, the term "heteroaryl group" may refer to an aryl group including 1 to 3 hetero atoms selected from N, O, S, P, and Si and remaining carbons in one functional group. When the heteroaryl group is a fused ring, each ring may include 1 to 3 hetero atoms.

More specifically, a substituted or unsubstituted C6 to C30 aryl group and/or a substituted or unsubstituted C2 to C30 heteroaryl group include a substituted or unsubstituted phenyl group, a substituted or unsubstituted naphthyl group, a substituted or unsubstituted anthracenyl group, a substituted or unsubstituted phenanthrylene group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, a combination thereof or a fused combination thereof, but is not limited thereto.

In the specification, hole characteristics refer to characteristics capable of donating an electron to form a hole when electric field is applied, and characteristics that hole formed in the anode is easily injected into the emission layer and transported in the emission layer due to conductive characteristics according to HOMO level.

In addition, electron characteristics refer to characteristics capable of accepting an electron to form a hole when electric field is applied, and characteristics that electron formed in the cathode is easily injected into the emission layer and transported in the emission layer due to conductive characteristics according to LUMO level.

Hereinafter, a compound for an organic optoelectric device according to one embodiment is described.

In one embodiment of the present invention, a compound for an organic optoelectric device represented by the following Chemical Formula I is provided.

[Chemical Formula I]

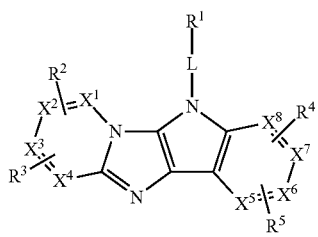

In the Chemical Formula I, $X^1$ to $X^8$ are independently N, C or $CR^a$,

L is a single bond, a substituted or unsubstituted C1 to C30 alkylene group, a substituted or unsubstituted C3 to C30 cycloalkylene group, a substituted or unsubstituted C3 to C30 heterocycloalkylene group, a substituted or unsubstituted C6 to C30 arylene group, or a substituted or unsubstituted C2 to C30 heteroarylene group, a substituted or unsubstituted C6 to C30 aryleneamine group, a substituted or unsubstituted C2 to C30 heteroaryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, $R^1$ is a substituted or unsubstituted C6 to C30 aryl group, a substituted or unsubstituted C2 to C30 heteroaryl group, or a combination thereof, $R^2$ to $R^5$ and $R^a$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C2 to C30 heteroarylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted C3 to C40 silyl group, a substituted or unsubstituted C3 to C40 silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C6 to C30 arylthiol group, a substituted or unsubstituted C1 to C30 heteroarylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof, and the $R^2$ and $R^3$, or $R^4$ and $R^5$ are independently present, or are fused to each other to provide a ring.

The compound for an organic optoelectric device represented by the Chemical Formula I includes a backbone in which a 6-membered ring moiety consisting of $X^1$ to $X^4$, an imidazoline moiety, a pyrrole moiety and a 6-membered ring moiety consisting of $X^5$ to $X^8$ are sequentially fused.

In particular, since one N of two "N's" of the imidazoline moiety is shared with the 6-membered ring moiety consisting of $X^1$ to $X^4$ in the compound for an organic optoelectric device represented by the Chemical Formula I, the 6-membered ring moiety consisting of $X^1$ to $X^4$ may be conjugated with the imidazoline moiety due to an unshared electron pair of the N.

The conjugation effect increases hole characteristics due to resonance stabilization when holes are injected. In other words, stability for holes is increased.

In addition, since the other N is not shared with the 6-membered ring moiety consisting of X1 to X4 but connected thereto due to a single bond and double bond, the compound includes no particular substituent. In this way, the compound includes no particular substituent and thus, may have a lower molecular weight and increased deposit process stability and resultantly, an effect on improving thermal resistance stability.

Since the backbone formed by sequentially fusing the 6-membered ring moiety consisting of $X^1$ to $X^4$, the imidazoline moiety, the pyrrole moiety and the 6-membered ring moiety consisting of $X^5$ to $X^8$ is a structure easily receiving holes, a compound for an organic optoelectric device may be designed to have strong hole characteristics by introducing a substituent easily receiving holes.

In addition, a bipolar structure may be formed by introducing a substituent easily receiving electrons.

A compound for an organic optoelectric device having the bipolar structure may appropriately balance hole and electron flows and thus, improve efficiency of an organic optoelectric device.

In addition, the compound has a low molecular weight as well as the bipolar characteristics and thus, may be deposited at a relatively low temperature and realize an organic optoelectric device having an excellent long life-span.

The Chemical Formula I may be specifically represented by one of the following Chemical Formulae 1 to 4.

[Chemical Formula 1]

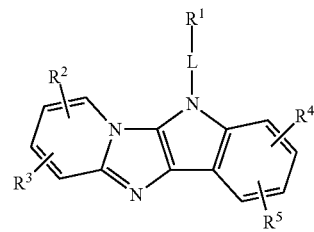

-continued

[Chemical Formula 2]

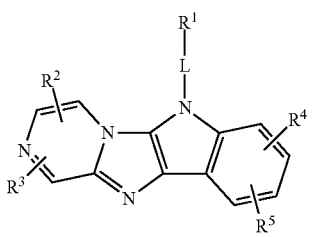

[Chemical Formula 3]

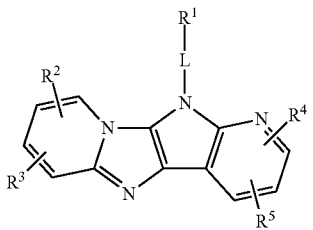

[Chemical Formula 4]

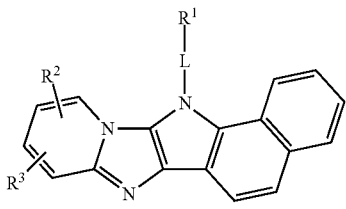

In the Chemical Formulae 1 to 4, L, $R^1$ to $R^5$ are the same as described above.

The Chemical Formula I may be more specifically represented by one of the following Chemical Formulae 5 to 8.

[Chemical Formula 5]

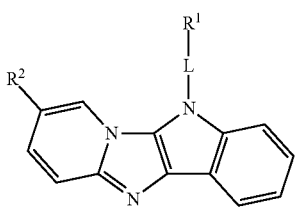

[Chemical Formula 6]

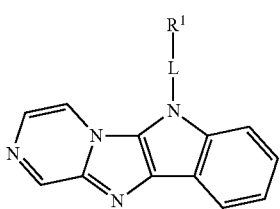

[Chemical Formula 7]

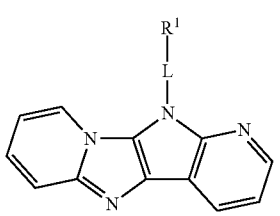

[Chemical Formula 8]

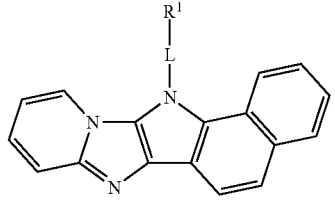

In the Chemical Formulae 5 to 8, L, $R^1$ and $R^2$ are the same as described above.

The compound for an organic optoelectric device represented by the Chemical Formula I may have desirable characteristics by adjusting the substituents $R^1$ to $R^5$.

For example, the $R^1$ may be one of moieties listed in the following Group I.

[Group I]

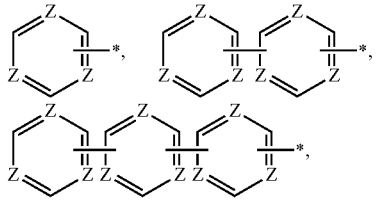

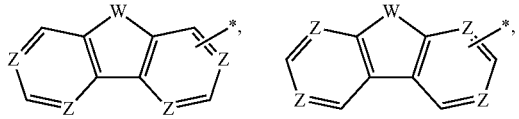

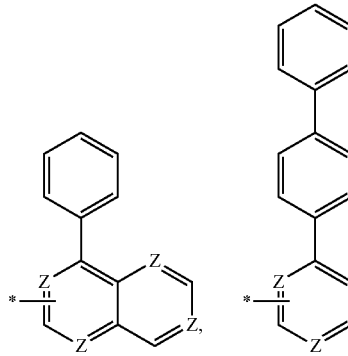

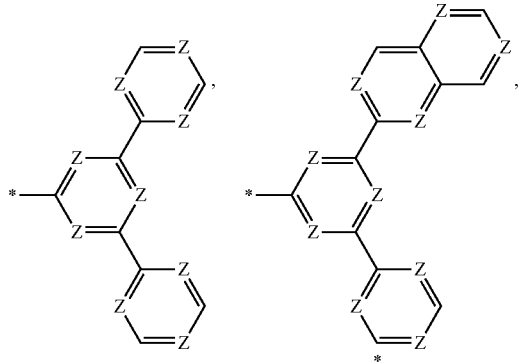

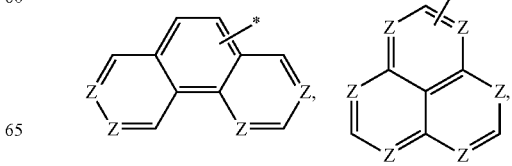

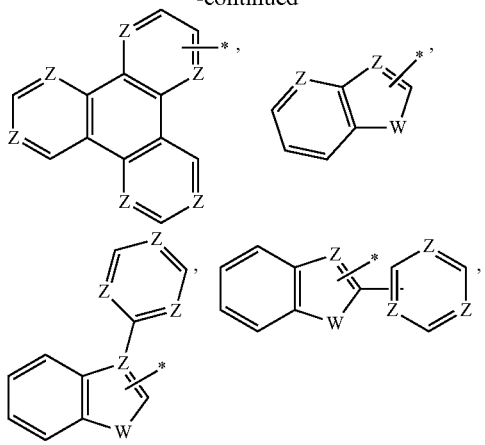

In the Group I,

Z are independently N or CR$^b$, at least one of Z is N,

W is NR$^c$, O, S, SO, SO$_2$, CR$^d$R$^e$, or SiR$^f$R$^g$, wherein R$^b$ to R$^g$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and \* is a linking point and may be positioned at one of element consisting of the functional groups.

The moieties listed in the Group I as a substituent may provide a compound for an organic optoelectric device having strong hole characteristics.

Specifically, the moieties listed in the Group I may be represented by one of moieties listed in the following Group I-1.

[Group I-1]

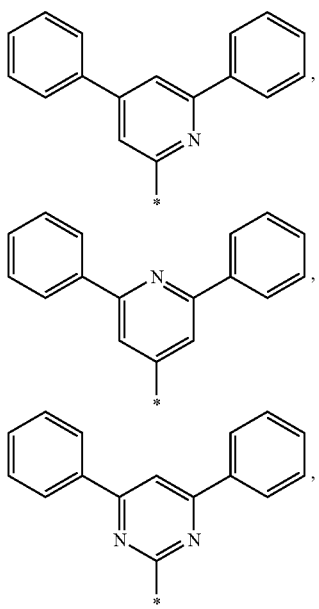

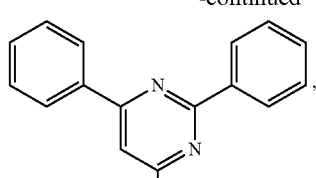

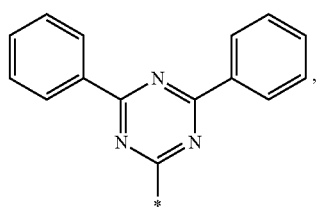

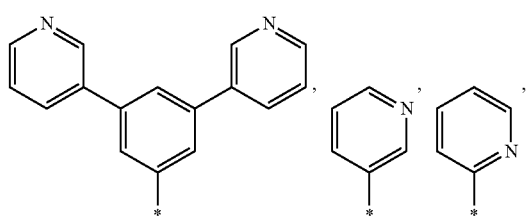

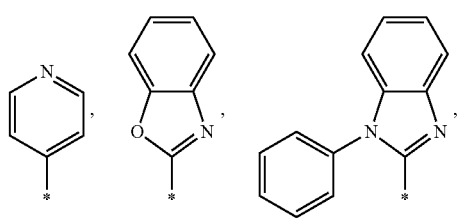

In the Group I-1. \* is a linking point.

In addition, the R$^1$ may be one of moieties of the following Group II.

[Group II]

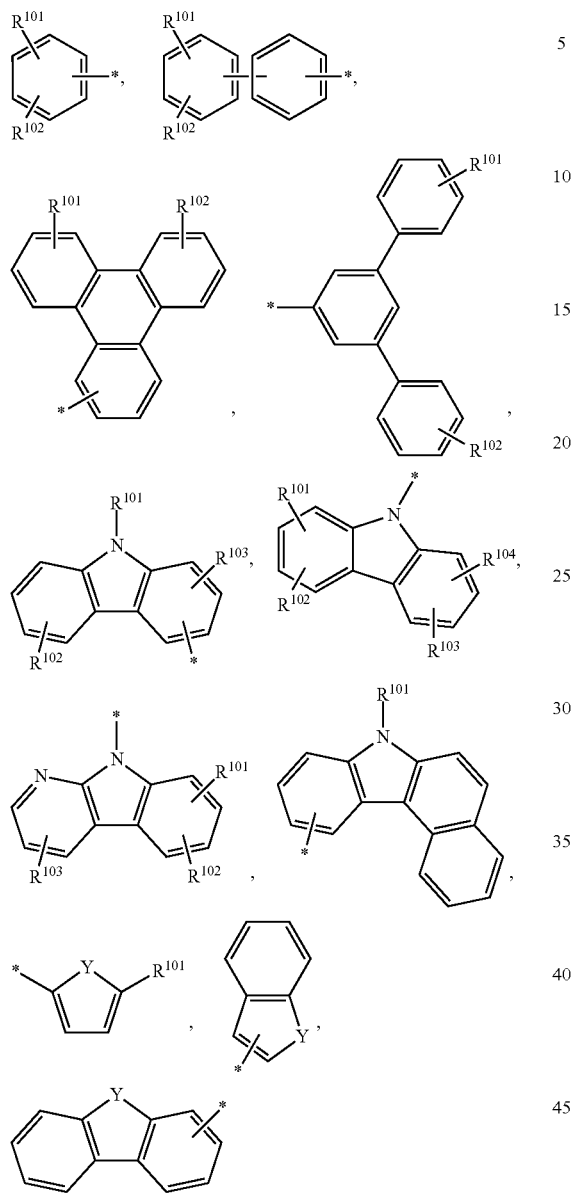

[Group II-1]

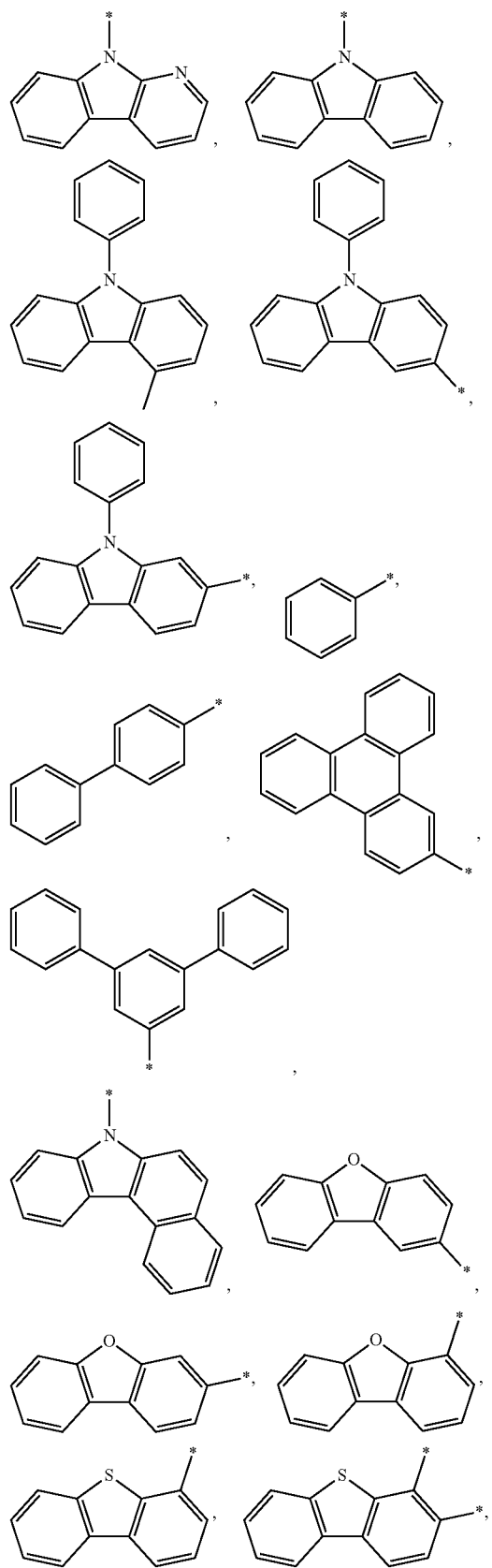

In the Group II, $R^{101}$ to $R^{104}$ are independently hydrogen, deuterium, a substituted or unsubstituted C1 to C30 alkyl group, a substituted or unsubstituted C1 to C30 silyl group, a substituted or unsubstituted C6 to C30 aryl group, or a combination thereof, Y is O, S, SO, or $SO_2$, and

* is a linking point and may be positioned at one of element consisting of the functional groups.

The moieties listed in the Group II as a substituent may provide a compound for an organic optoelectric device having bipolar characteristics.

Specifically, the moieties listed in the Group II may be represented by one of moieties listed in the following Group II-1.

[Group I-2]

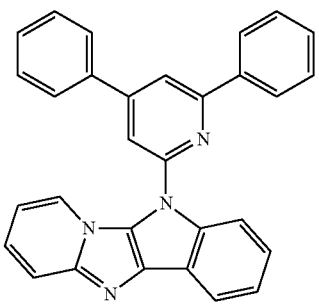
A-1

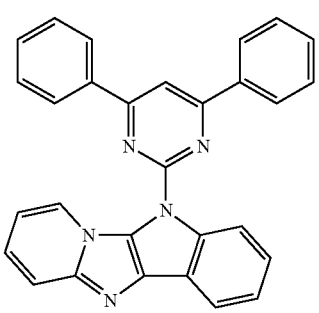
A-2

A-3

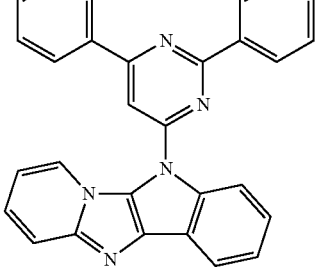
A-4

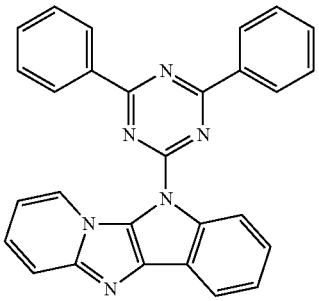
A-5

-continued

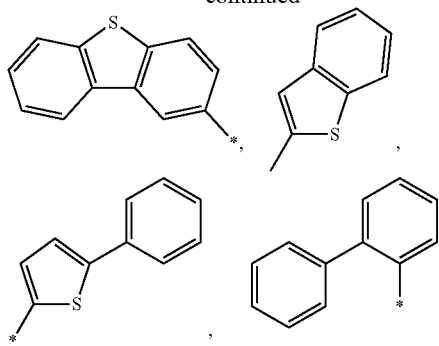

In the Group II-1, * is a linking point.
C6 to C30 arylene group, a substituted or unsubstituted C2 to C30 heteroarylene group, or a combination thereof.

The substituted or unsubstituted C6 to C30 arylene group, or the substituted or unsubstituted C2 to C30 heteroarylene group may be a substituted or unsubstituted phenylene group, a substituted or unsubstituted biphenylene group, a substituted or unsubstituted terphenylene group, a substituted or unsubstituted pyridylene group, or a combination thereof.

Specifically, the substituted or unsubstituted phenylene group, or the substituted or unsubstituted pyridylene group may be one of moieties of the following Group III.

[Group III]

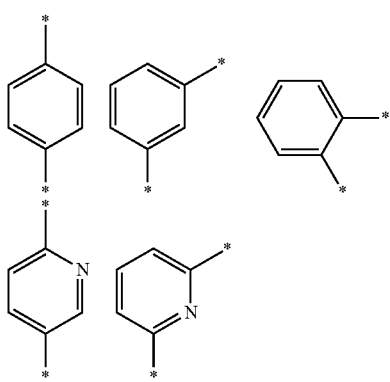

In the Group III, * is a linking point.

The compound for an organic optoelectric device may be applied to an organic optoelectric device at alone or with a compound for an organic optoelectric device. The compound for an organic optoelectric device is used with another compound for an organic optoelectric device as a composition.

Hereinafter, examples of a composition for an organic optoelectric device including the compound for an organic optoelectric device are described.

As an example of the composition for an organic optoelectric device, a compound including one of moieties listed in the Group I as a substituent is referred to as "a first compound for an organic optoelectric device", and a compound including one of moieties listed in the group II is referred to as "a second compound for an organic optoelectric device" of the organic compounds.

The first compound for an organic optoelectric device may be, for example compounds listed in the following Group I-2, but is not limited thereto.

-continued
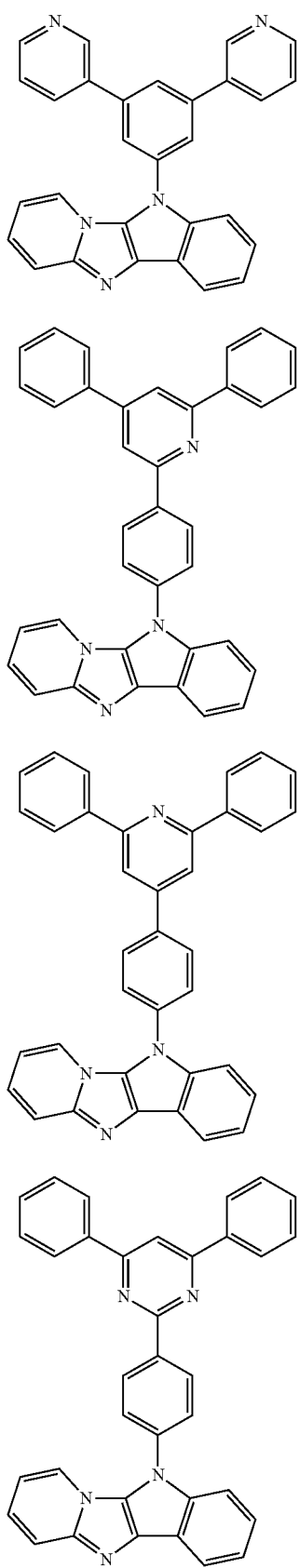
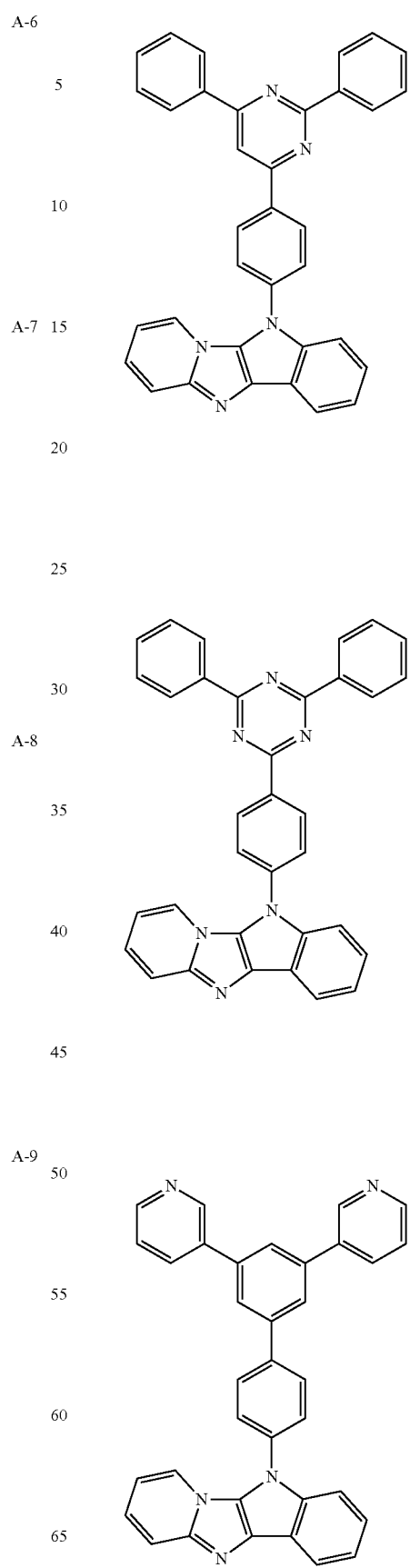

-continued
A-13
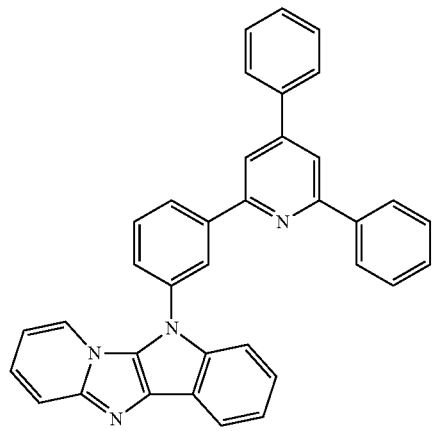
A-14
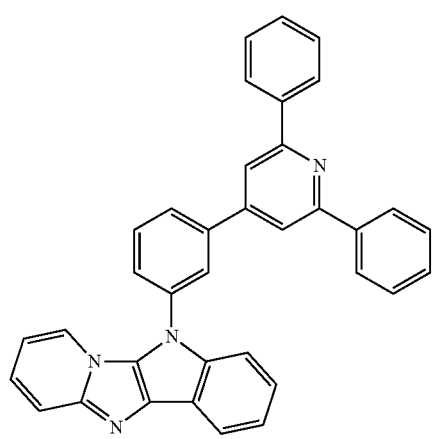
A-15
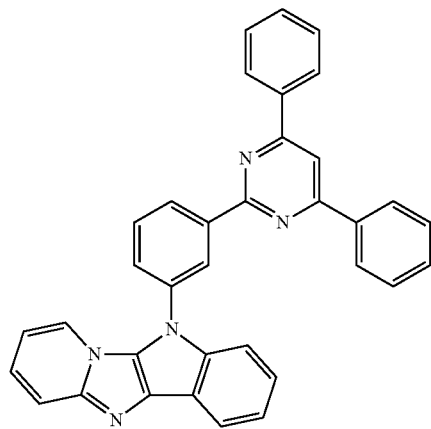
-continued
A-16
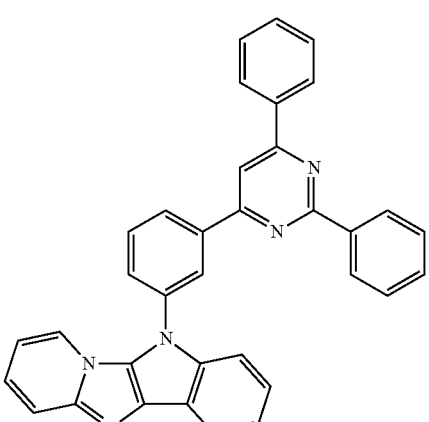
A-17
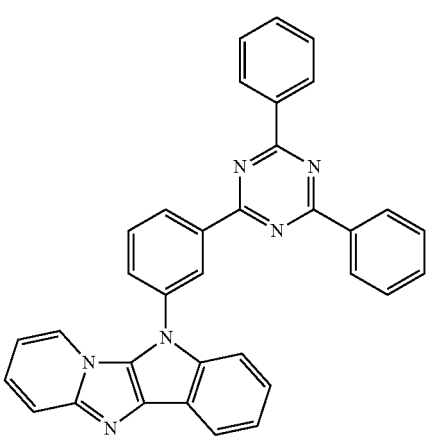
A-18
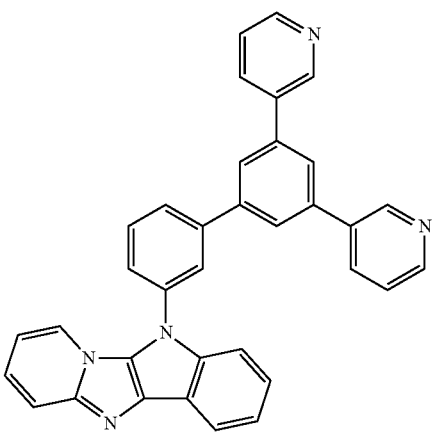
A-19
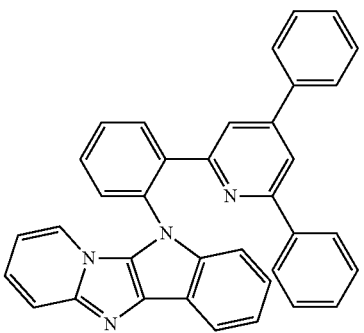

A-20 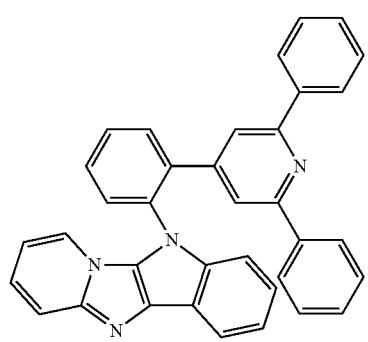
A-21 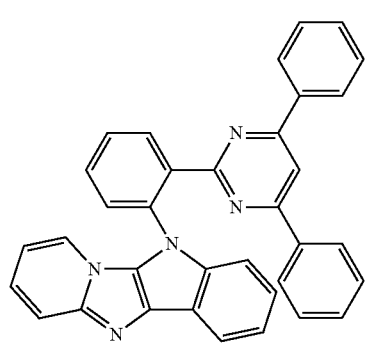
A-22 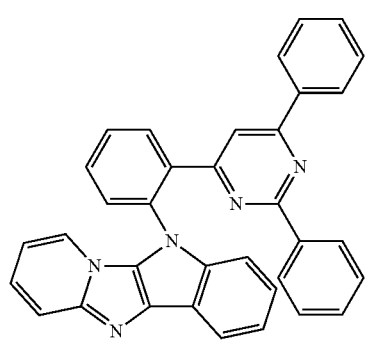
A-23 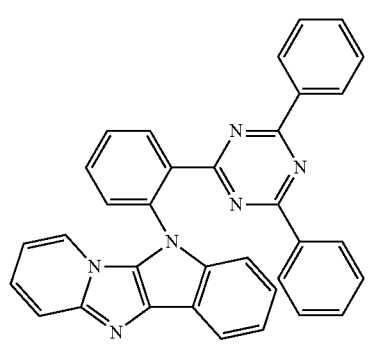
A-24 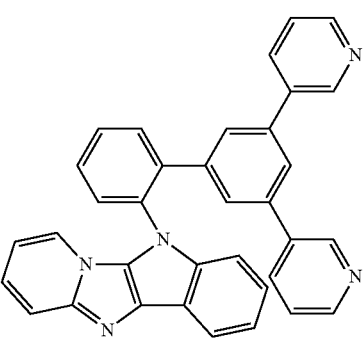
A-25 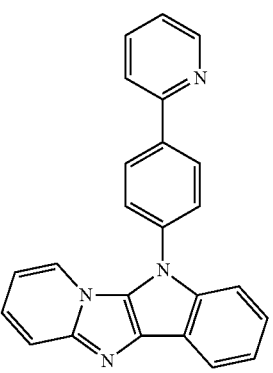
A-26 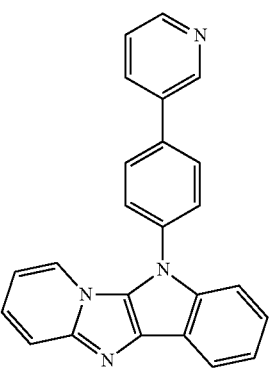
A-27 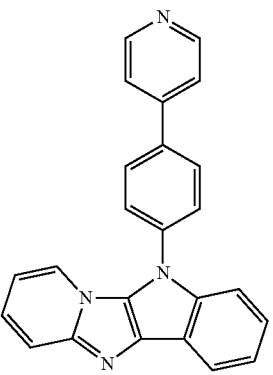

A-28 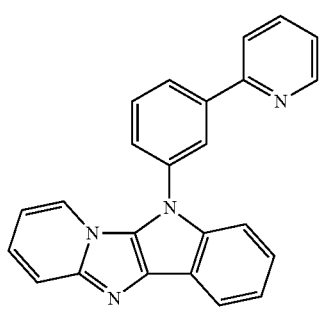
A-29 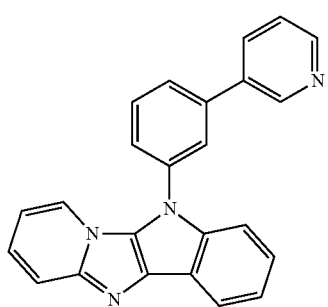
A-30 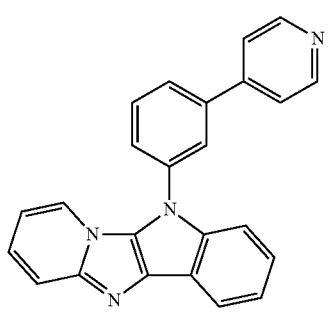
A-31 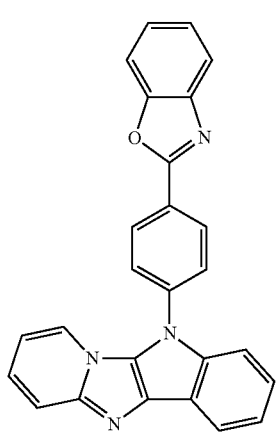
A-32 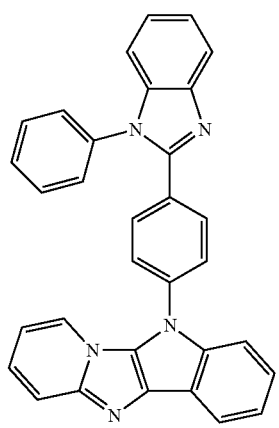
A-33 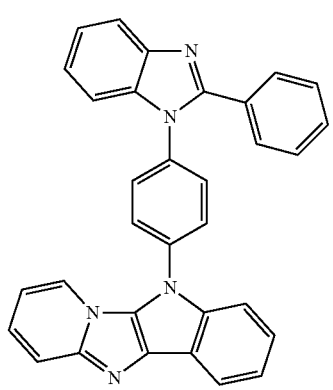
A-34 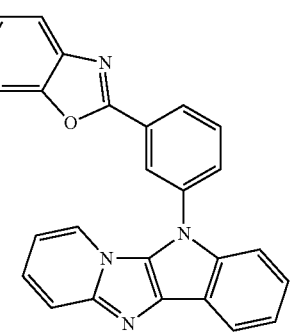
A-35 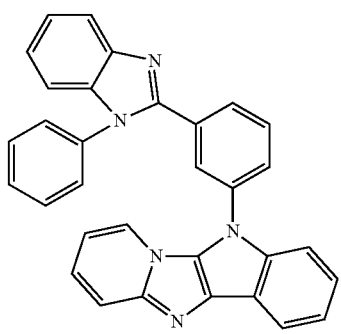

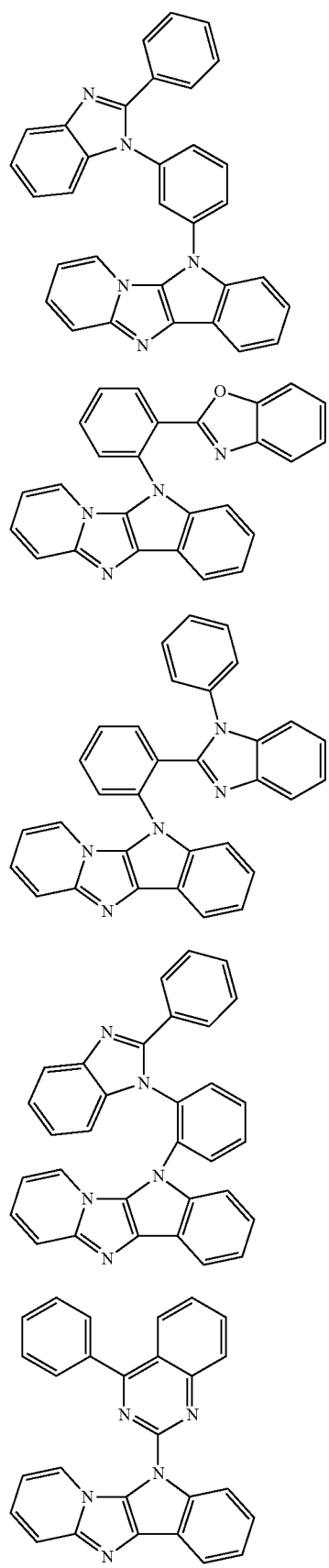
A-36
A-37
A-38
A-39
A-40
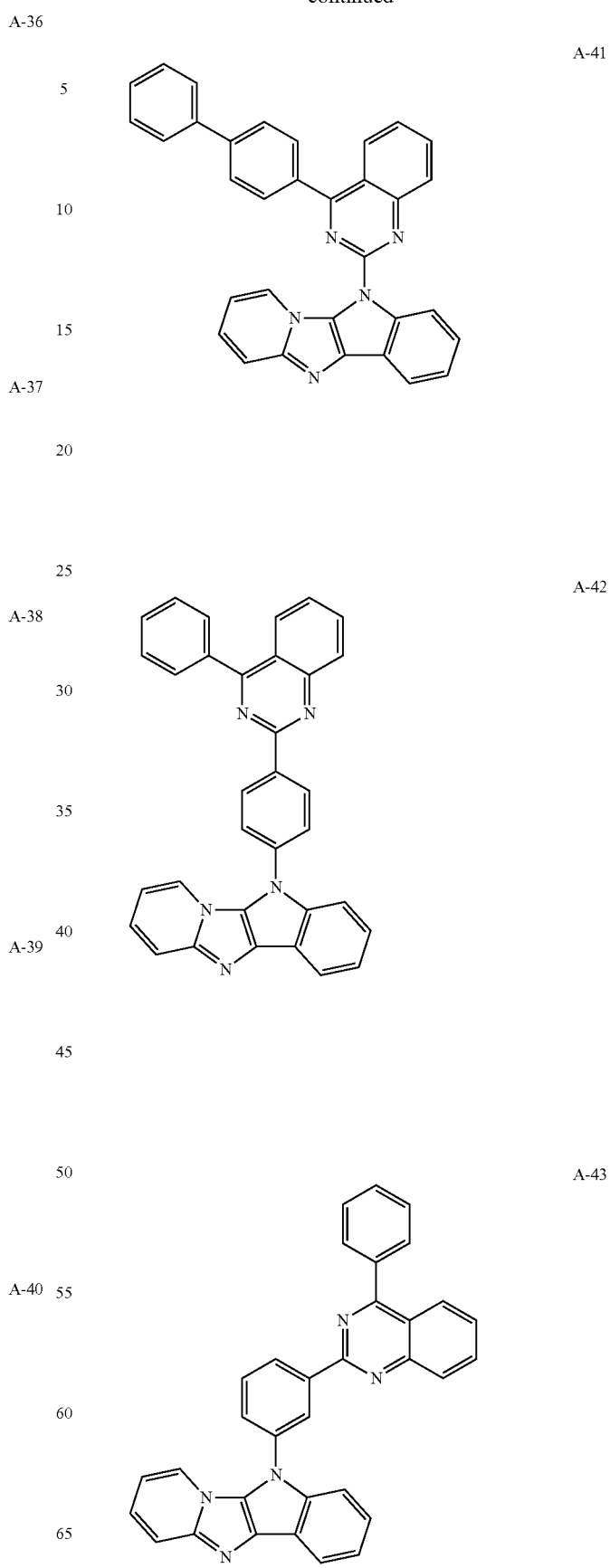
A-41
A-42
A-43

A-44
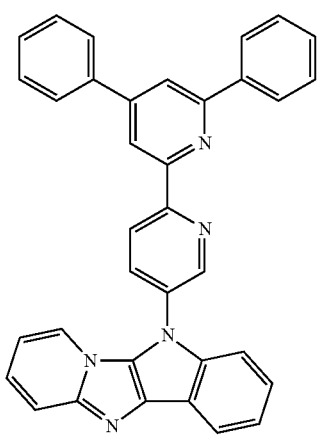
A-45
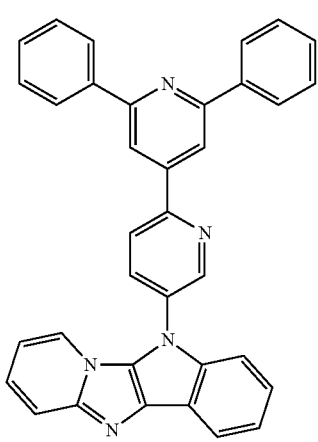
A-46
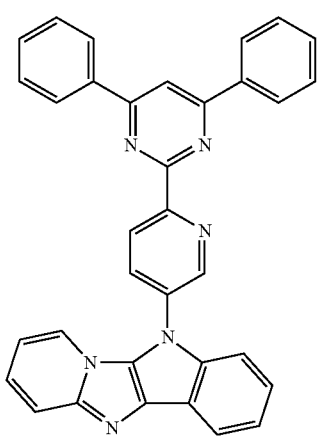
A-47
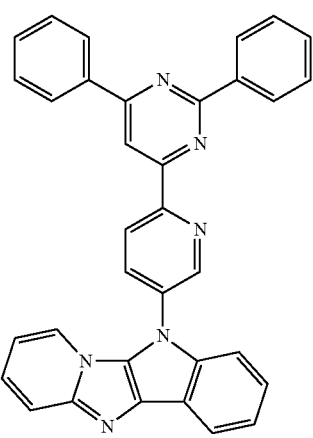
A-48
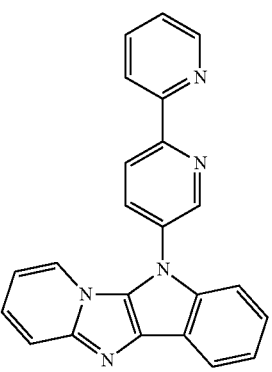
A-49
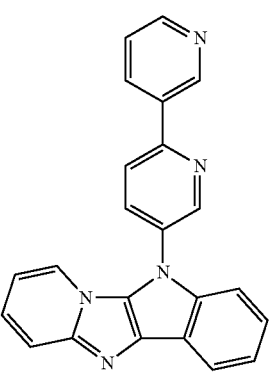
A-50
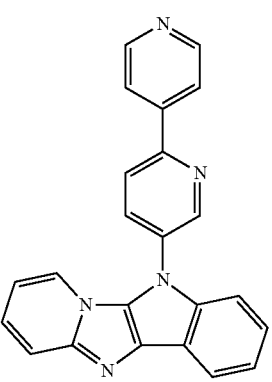

A-51 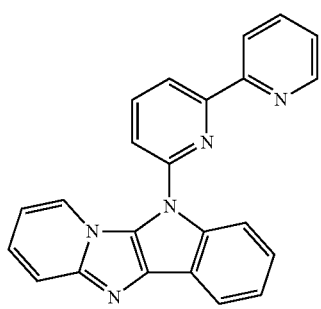
A-52 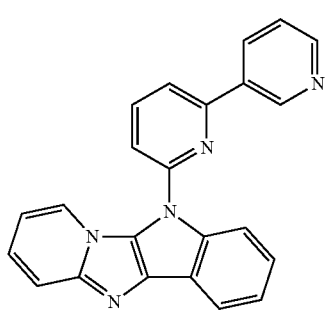
A-53 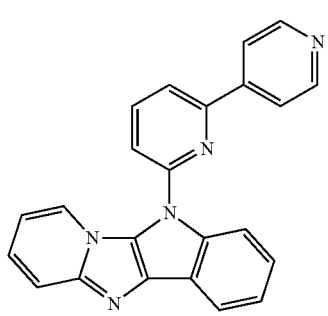
A-54 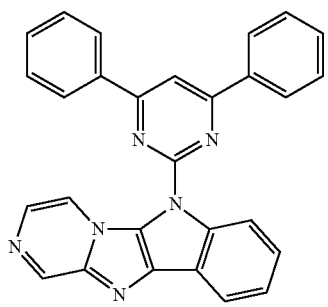
A-55 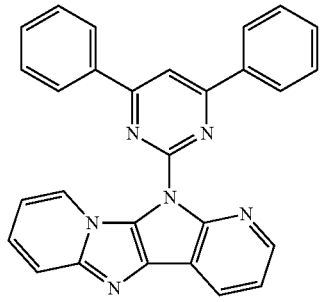
A-56 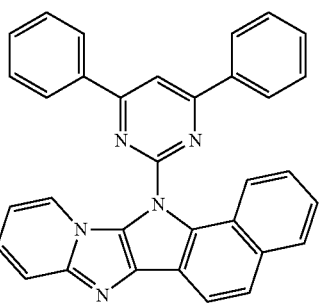
The second compound for an organic optoelectric device may be, for example compounds listed in the following Group II-2, but is not limited thereto.
[Group II-2]
B-1 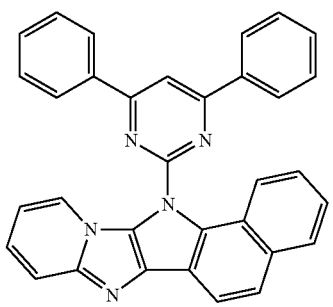
B-2 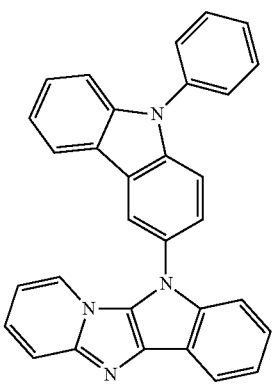
B-3 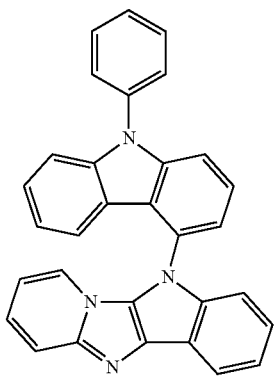

-continued
B-4 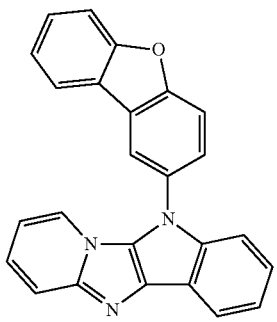
B-5 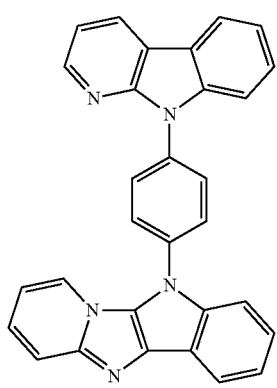
B-6 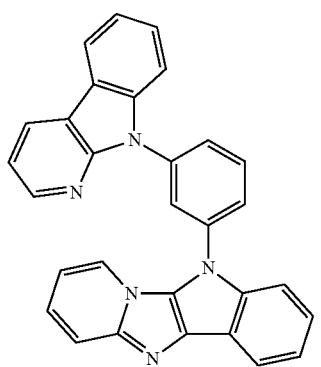
B-7 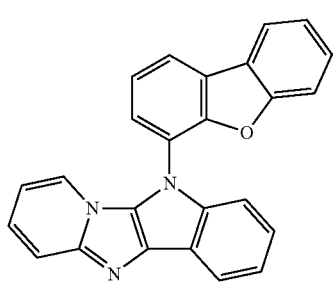
-continued
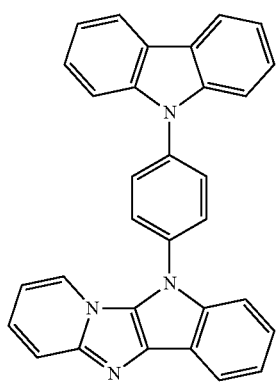
B-8
B-9 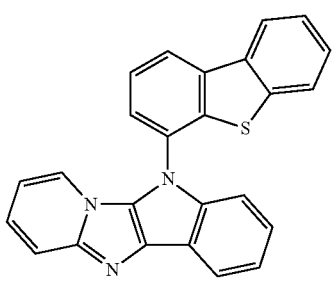
B-10 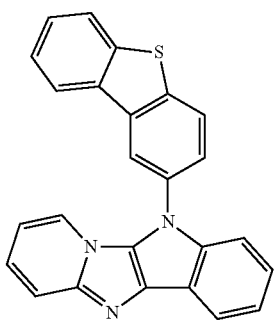
B-11 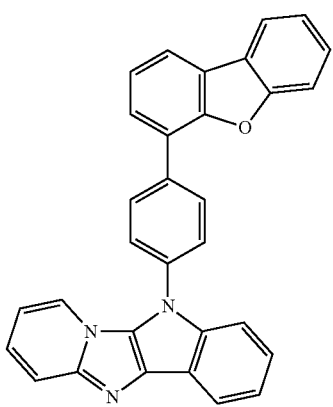

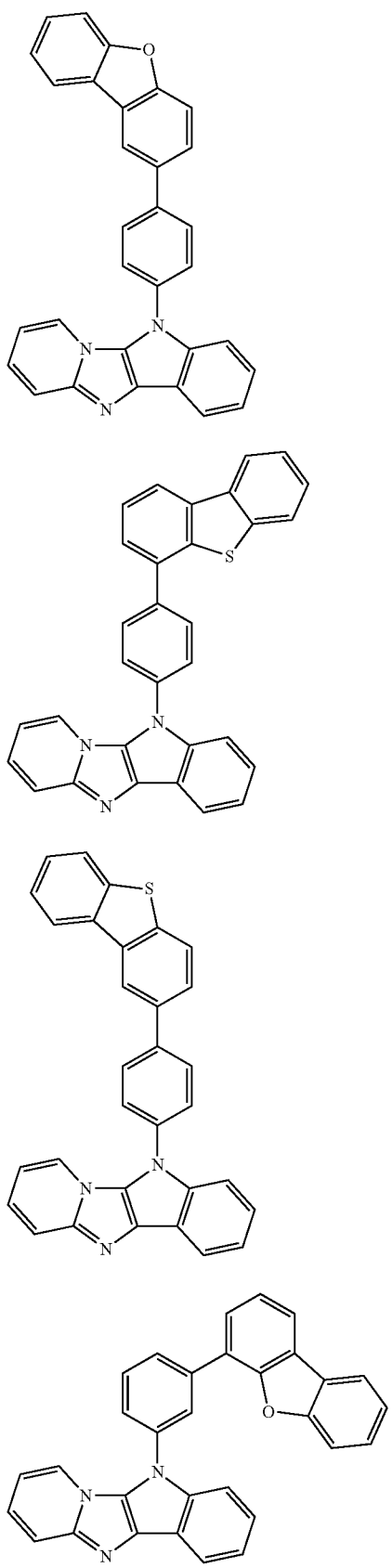
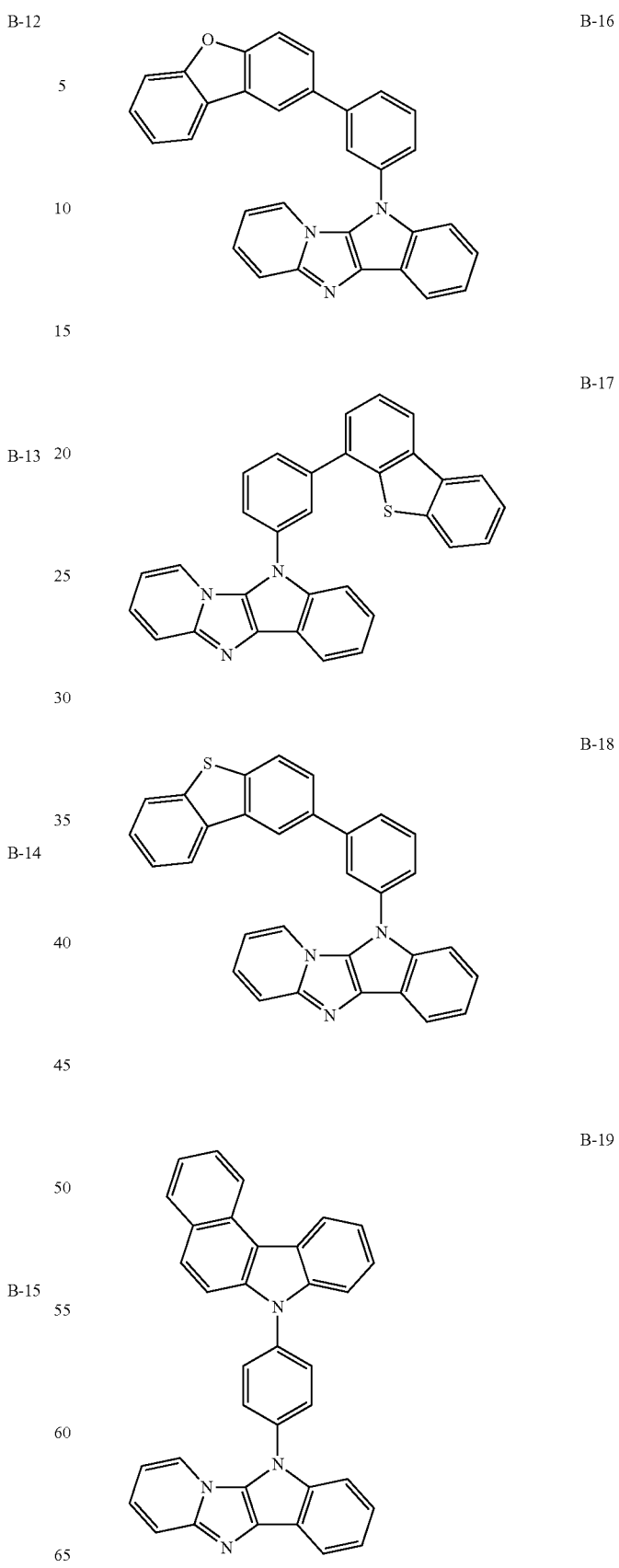

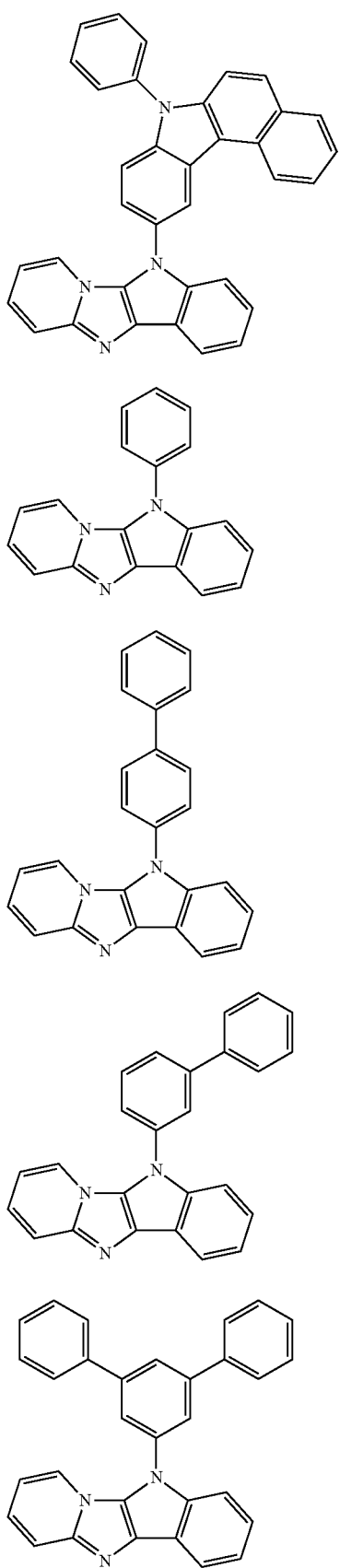
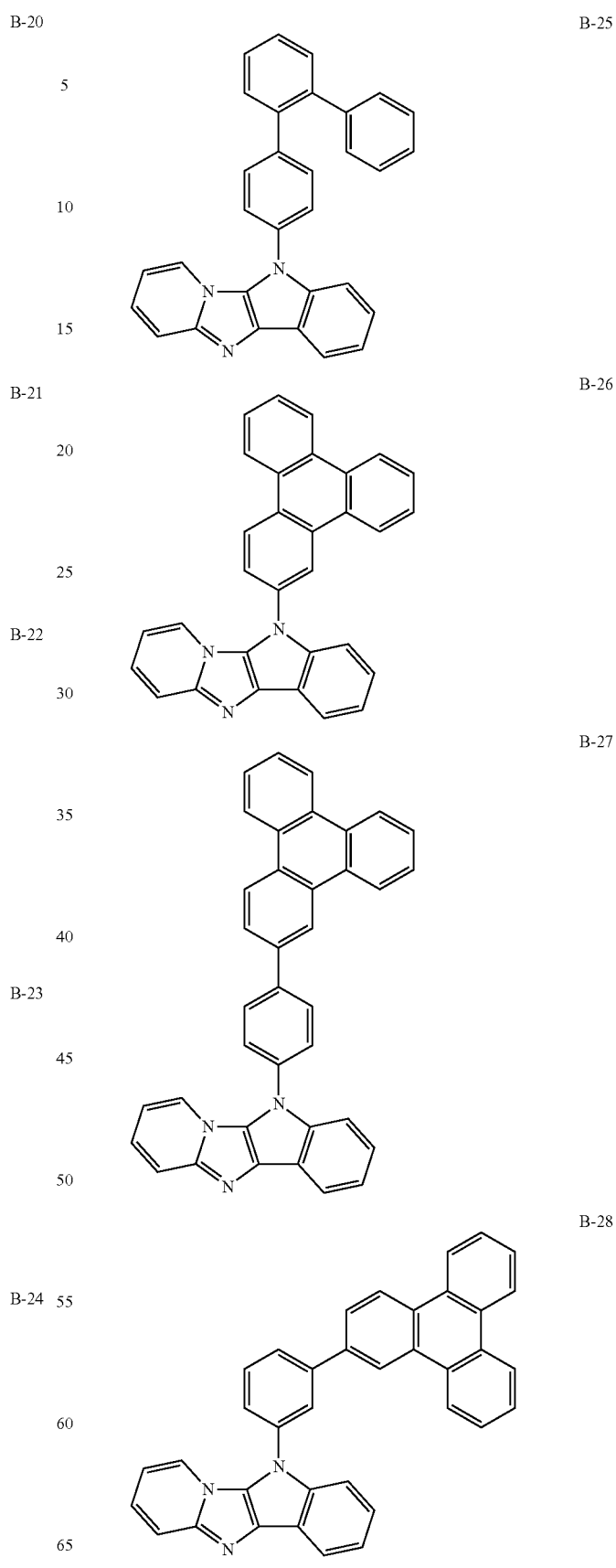

B-29 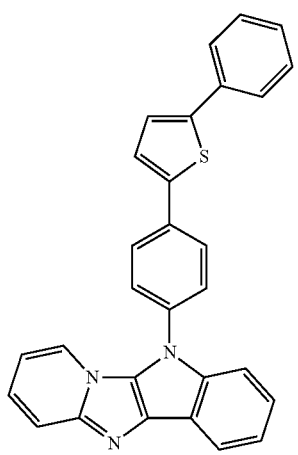
B-30 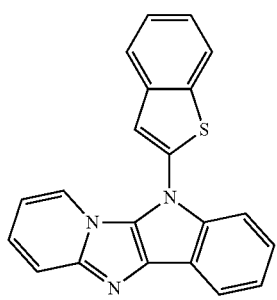
B-31 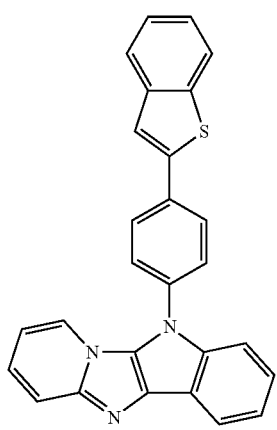
B-32 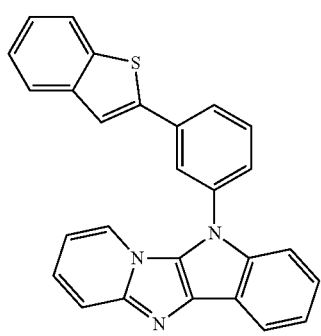
B-33 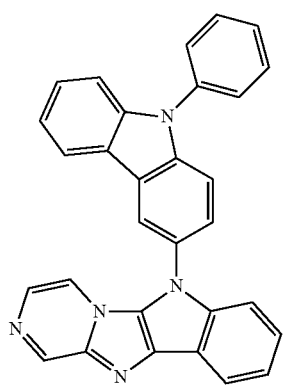
B-34 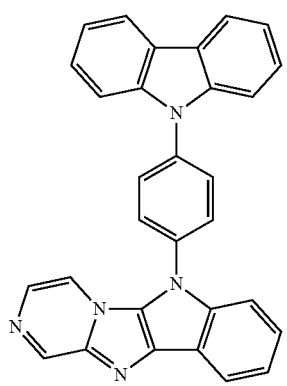
B-35 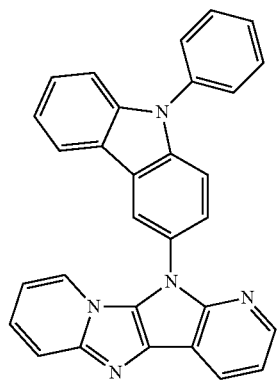
B-36 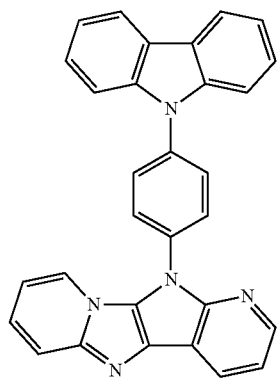

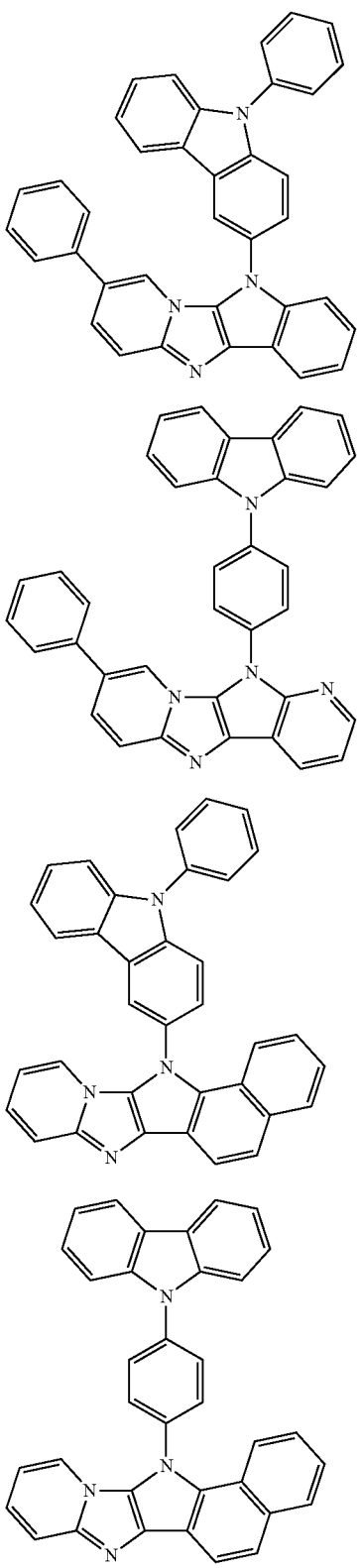

The composition may include the first compound for an organic optoelectric device and the second compound for an organic optoelectric device in a weight ratio of about 1:10 to about 10:1.

The first compound for an organic optoelectric device and the second compound for an organic optoelectric device may be used as a first host compound and a second host compound respectively and may further include a dopant. The dopant may be a red, green, or blue dopant.

The dopant is mixed with the first host compound and the second host compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

Examples of the dopant may be a phosphorescent dopant, and examples of the phosphorescent dopant may be an organic metal compound including Ir, Pt, Os, Ti, Zr, Hf, Eu, Tb, Tm, Fe, Co, Ni, Ru, Rh, Pd or a combination thereof. The phosphorescent dopant may be, for example a compound represented by the following Chemical Formula Z, but is not limited thereto.

$$L_2MX \qquad \text{[Chemical Formula Z]}$$

In the Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand.

The composition may form a film using a dry film-forming method such as chemical vapor deposition.

Hereinafter, an organic optoelectric device to which the organic compound or the composition is applied is described.

The organic optoelectric device may be any device to convert electrical energy into photoenergy and vice versa without particular limitation, and may be, for example an organic photoelectric device, an organic light emitting diode, an organic solar cell, and an organic photo-conductor drum.

The organic optoelectric device includes an anode and a cathode facing each other, and at least one organic layer interposed between the anode and the cathode, wherein the organic layer includes the above organic compound or composition.

Herein, an organic light emitting diode as one example of an organic optoelectric device is described referring to drawings.

Figure 2:
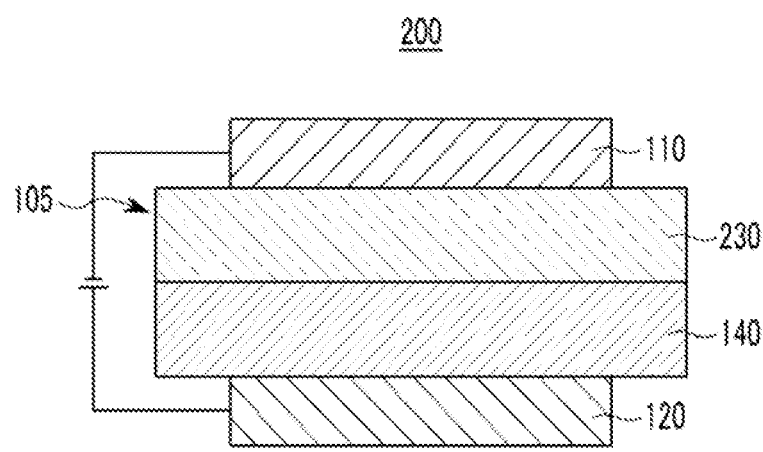

FIGS. 1 and 2 are cross-sectional views of each organic light emitting diode according to one embodiment.

Referring to FIG. 1, an organic optoelectric device 100 according to one embodiment includes an anode 120 and a cathode 110 facing each other and an organic layer 105 interposed between the anode 120 and cathode 110.

The anode 120 may be made of a conductor having a large work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example metal, metal oxide and/or a conductive polymer.

The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO$_2$/Al, LiF/Ca, LiF/Al and BaF$_2$/Ca, but is not limited thereto.

The organic layer 105 includes an emission layer 130 including the compound for an organic optoelectric device or the above composition for an organic optoelectric device.

The emission layer 130 may include for example the above organic compound at alone, a mixture of at least two kinds of the above organic compound, or the composition.

Referring to FIG. 2, an organic light emitting diode 200 further includes a hole auxiliary layer 140 as well as an emission layer 230. The hole auxiliary layer 140 may further increase hole injection and/or hole mobility between the anode 120 and emission layer 230 and block electrons. The hole auxiliary layer 140 may be, for example a hole transport layer (HTL), a hole injection layer (HIL), and/or an electron blocking layer, and may include at least one layer.

In one embodiment of the present invention, an organic light emitting diode may further include an electron transport layer (ETL), an electron injection layer (EIL), a hole injection layer (HIL), and the like, as an organic layer 105 in FIG. 1 or FIG. 2.

The organic light emitting diodes 100 and 200 may be manufactured by forming an anode or a cathode on a substrate, forming an organic layer in accordance with a dry coating method such as evaporation, sputtering, plasma plating, and ion plating; and forming a cathode or an anode thereon.

The organic light emitting diode may be applied to an organic light emitting diode (OLED) display.

Hereinafter, the embodiments are illustrated in more detail with reference to examples. However, the present disclosure is illustrated in more detail with reference to examples.

Preparation of Compound for Organic Optoelectric Device

Example 1: Synthesis of Compound A-3

A compound A-3 as specific examples of a compound for an organic optoelectric device of the present invention was synthesized through the following Reaction Scheme.

[Reaction Scheme 1]

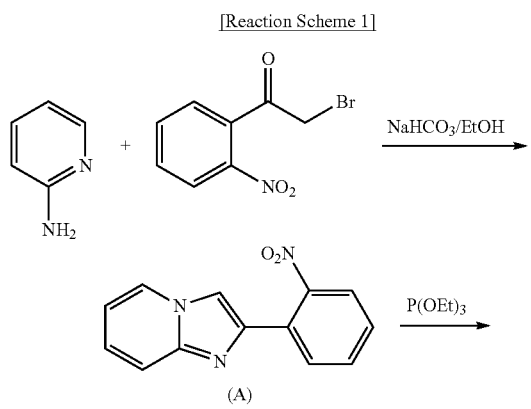

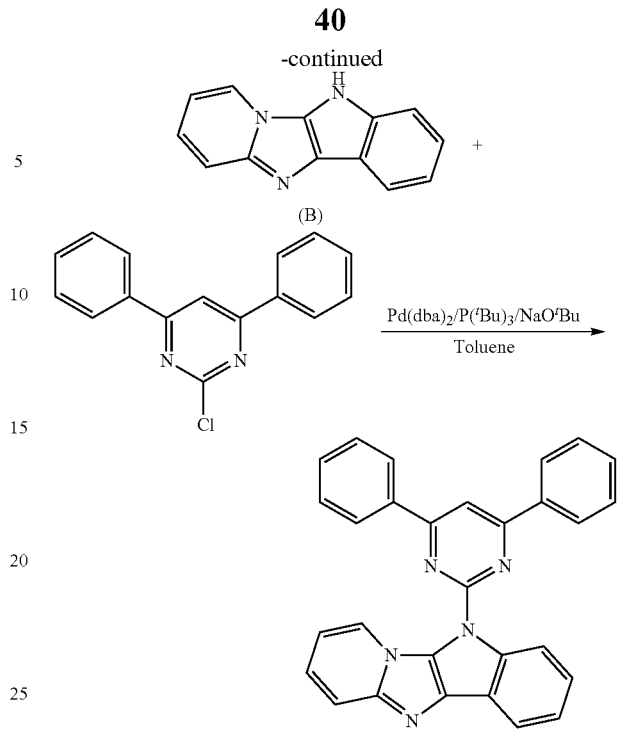

First Step; Synthesis of Intermediate Product (A)

20.0 g (212.5 mmol) of 2-aminopyridine, 51.9 g (212.5 mmol) of 2-bromo-1-(2-nitrophenyl)-ethanone, and 17.85 g (212.5 mmol) of sodium bicarbonate (NaHCO$_3$) were dissolved in 400 mL of ethanol, and the solution was refluxed and agitated under a nitrogen stream for 6 hours. When the reaction was complete, the ethanol was removed by using a revolving evaporator. 500 mL of water was added thereto, and the obtained mixture was agitated for 30 minutes and then, filtered. The obtained solid compound was recrystallized with ethanol, obtaining 36.0 g of an intermediate product A (a yield: 71%).

HRMS (70 eV, EI$^+$) m/z calcd for C13H9N3O2: 239.07. found for 239.42.

Second Step; Synthesis of Intermediate Product (B)

30.0 g (125.4 mmol) of the intermediate product A was dissolved in 200 mL of triethylphosphite (P(OEt)$_3$), and the solution was refluxed and agitated under a nitrogen stream for 12 hours. After the reaction was completed, the triethylphosphite was distilled and removed under a reduced pressure. The concentrated product was separated through column chromatography, obtaining 20 g (77%) of an intermediate product (B).

HRMS (70 eV, EI$^+$) m/z calcd for C13H9N3: 207.08. found for 207.43.

Third Step; Synthesis of Compound A-3

20.0 g (96.5 mmol) of the intermediate product (B), 30.9 g (115.8 mmol) of 2-chloro-4,6-diphenyl-pyrimidine, 13.9 g (144.8 mmol) of sodium t-butoxide (NaOtBu), 2.8 g (4.8 mmol) of Pd(dba)$_2$, and 5.8 g (50% in toluene) of tri t-butylphosphine (P(tBu)$_3$) were put in 400 mL of toluene, and the mixture was heated and refluxed under a nitrogen stream for 12 hours. The obtained mixture was added to 1000 mL of methanol to crystallize a solid, the solid was filtered, dissolved in toluene, filtered with silica gel/Celite, and then, recrystallized with methanol after removing an organic solvent in an appropriate amount, obtaining 35.0 g (83%) of a compound A-3.

HRMS (70 eV, EI+) m/z calcd for C29H19N5: 437.16. found for 437.51.

Example 2: Synthesis of Compound A-5

A compound A-5 as specific examples of a compound for an organic optoelectric device of the present invention was synthesized through the following Reaction Scheme.

[Reaction Scheme 2]

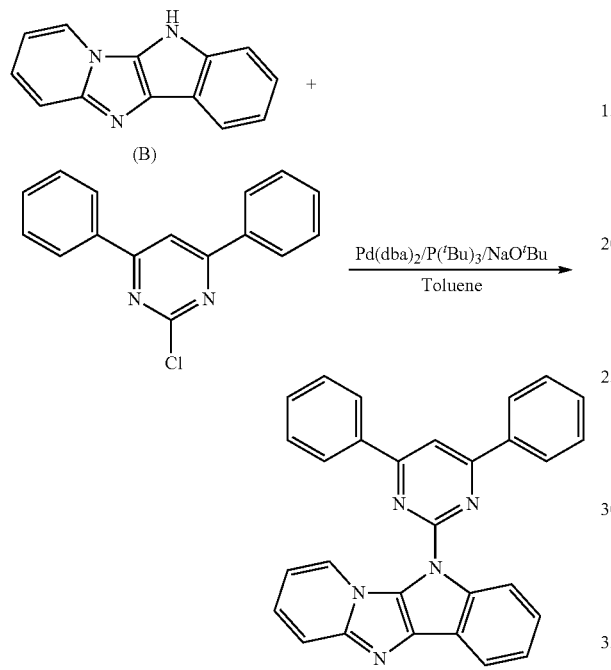

10.0 g (48.3 mmol) of the intermediate product (B), 15.5 g (57.9 mmol) of 2-chloro-4,6-diphenyl-[1,3,5]triazine, 6.9 g (72.4 mmol) of sodium t-butoxide (NaOtBu), 1.4 g (2.4 mmol) of Pd(dba)$_2$, and 2.9 g (50% in toluene) of tri t-butylphosphine (P(tBu)$_3$) were put in 200 mL of toluene, and the mixture was heated and refluxed under a nitrogen stream for 12 hours. The obtained mixture was added to 1000 mL of methanol to crystallize a solid, and the solid was filtered, dissolved in toluene, filtered with silica gel/Celite, and then, recrystallized after removing an appropriate amount of an organic solvent, obtaining 15.0 g (71%) of a compound A-5.

HRMS (70 eV, EI+) m/z calcd for C28H18N6: 438.16. found for 438.51.

Example 3: Synthesis of Compound A-15

A compound A-15 as specific examples of a compound for an organic optoelectric device of the present invention was synthesized through the following Reaction Scheme.

[Reaction Scheme 3]

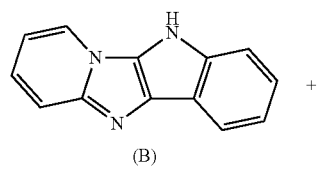

+

[Reaction Scheme 2 continued]

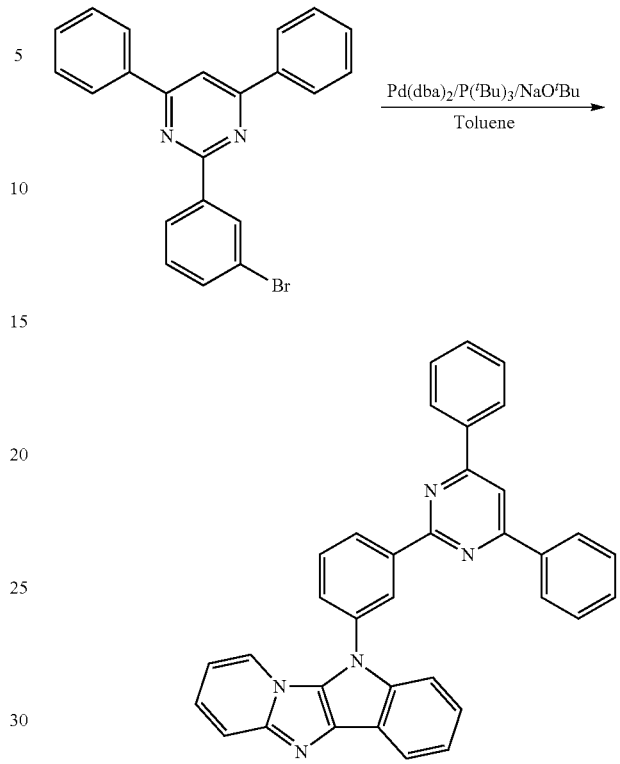

8.0 g (38.6 mmol) of the intermediate product (B), 17.9 g (46.3 mmol) of 2-(3-bromophenyl)-4,6-diphenyl-pyrimidine, 5.6 g (57.9 mmol) of sodium t-butoxide (NaOtBu), 1.1 g (1.9 mmol) of Pd(dba)$_2$, and 2.3 g (50% in toluene) of tri t-butylphosphine (P(tBu)$_3$) were put in 200 mL of toluene, and the mixture was heated and refluxed under a nitrogen stream for 12 hours. The obtained mixture was added to 1000 mL of methanol to crystallize a solid, and the solid was dissolved in toluene, filtered with silica gel/Celite, and then, recrystallized after removing an appropriate amount of an organic solvent, obtaining 15.0 g (76%) of a compound A-15.

HRMS (70 eV, EI+) m/z calcd for C35H23N5: 513.20. found for 513.55.

Example 4: Synthesis of Compound A-17

A compound A-17 as specific examples of a compound for an organic optoelectric device of the present invention was synthesized through the following Reaction Scheme.

[Reaction Scheme 4]

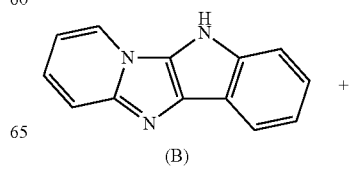

+

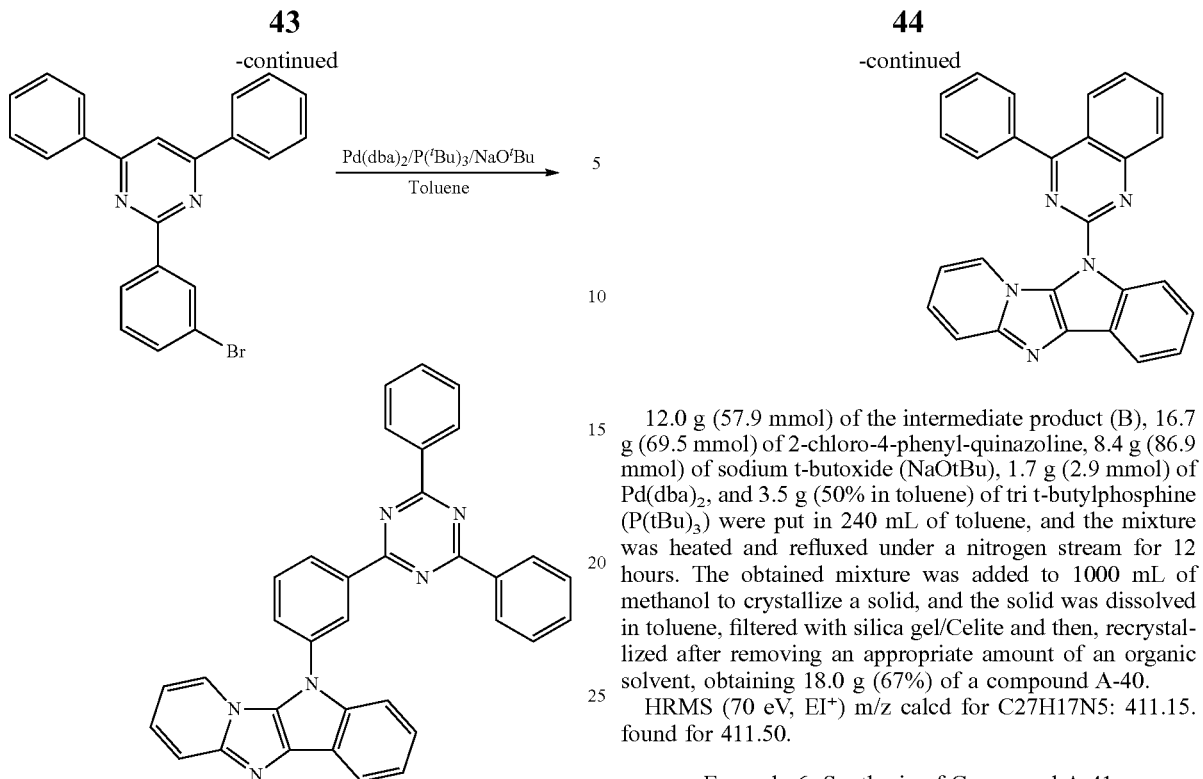

10.0 g (48.3 mmol) of the intermediate product (B), 22.5 g (57.9 mmol) of 2-(3-bromophenyl)-4,6-diphenyl-[1,3,5]triazine, 6.9 g (72.4 mmol) of sodium t-butoxide (NaOtBu), 1.4 g (2.4 mmol) of Pd(dba)$_2$, and 2.9 g (50% in toluene) of tri t-butylphosphine (P(tBu)$_3$) were put in 200 mL of toluene, and the mixture was heated and refluxed under a nitrogen stream for 12 hours. The obtained mixture was added to 1000 mL of methanol to crystallize a solid, and the solid was dissolved in toluene, filtered with silica gel/Celite, and then, recrystallized after removing an appropriate amount of an organic solvent, obtaining 18.0 g (72%) of a compound A-17.

HRMS (70 eV, EI$^+$) m/z calcd for C34H22N6: 514.19. found for 514.54.

Example 5: Synthesis of Compound A-40

A compound A-40 as specific examples of a compound for an organic optoelectric device of the present invention was synthesized through the following Reaction Scheme.

[Reaction Scheme 5]

12.0 g (57.9 mmol) of the intermediate product (B), 16.7 g (69.5 mmol) of 2-chloro-4-phenyl-quinazoline, 8.4 g (86.9 mmol) of sodium t-butoxide (NaOtBu), 1.7 g (2.9 mmol) of Pd(dba)$_2$, and 3.5 g (50% in toluene) of tri t-butylphosphine (P(tBu)$_3$) were put in 240 mL of toluene, and the mixture was heated and refluxed under a nitrogen stream for 12 hours. The obtained mixture was added to 1000 mL of methanol to crystallize a solid, and the solid was dissolved in toluene, filtered with silica gel/Celite and then, recrystallized after removing an appropriate amount of an organic solvent, obtaining 18.0 g (67%) of a compound A-40.

HRMS (70 eV, EI$^+$) m/z calcd for C27H17N5: 411.15. found for 411.50.

Example 6: Synthesis of Compound A-41

A compound A-41 as specific examples of a compound for an organic optoelectric device of the present invention was synthesized through the following Reaction Scheme.

[Reaction Scheme 6]

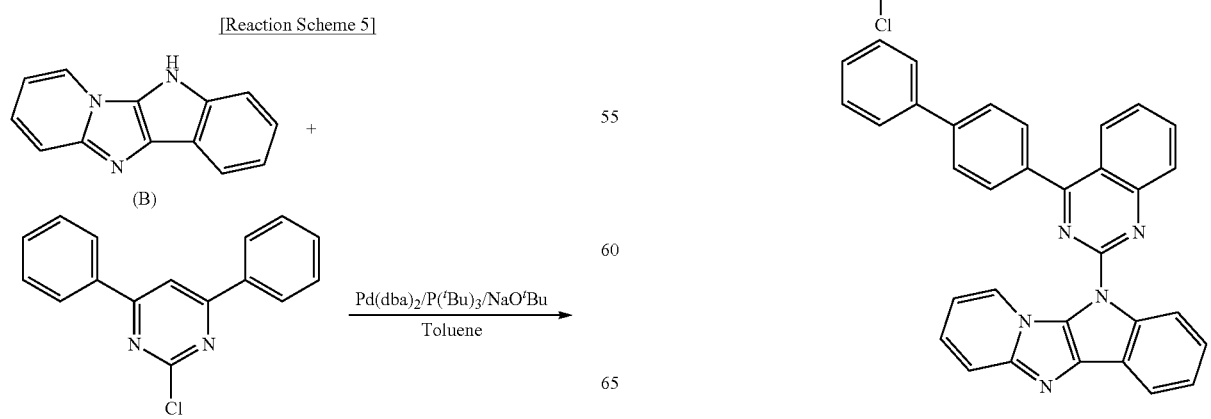

10.0 g (48.3 mmol) of the intermediate product (B), 18.3 g (57.9 mmol) of 4-biphenyl-4-yl-2-chloro-quinazoline, 6.9 g (72.4 mmol) of sodium t-butoxide (NaOtBu), 1.4 g (2.4 mmol) of Pd(dba)$_2$, and 2.9 g (50% in toluene) of tri t-butylphosphine (P(tBu)$_3$) were put in 200 mL of toluene, and the mixture was heated and refluxed under a nitrogen stream for 12 hours. The obtained mixture was added to 1000 mL of methanol to crystallize a solid, and the solid was filtered, dissolved in toluene, filtered with silica gel/Celite, and then, recrystallized after removing an appropriate amount of an organic solvent, obtaining 18.0 g (77%) of a compound A-41.

HRMS (70 eV, EI$^+$) m/z calcd for C33H21N5: 487.18. found for 487.53.

Example 7: Synthesis of Compound A-43

A compound A-43 as specific examples of a compound for an organic optoelectric device of the present invention was synthesized through the following Reaction Scheme.

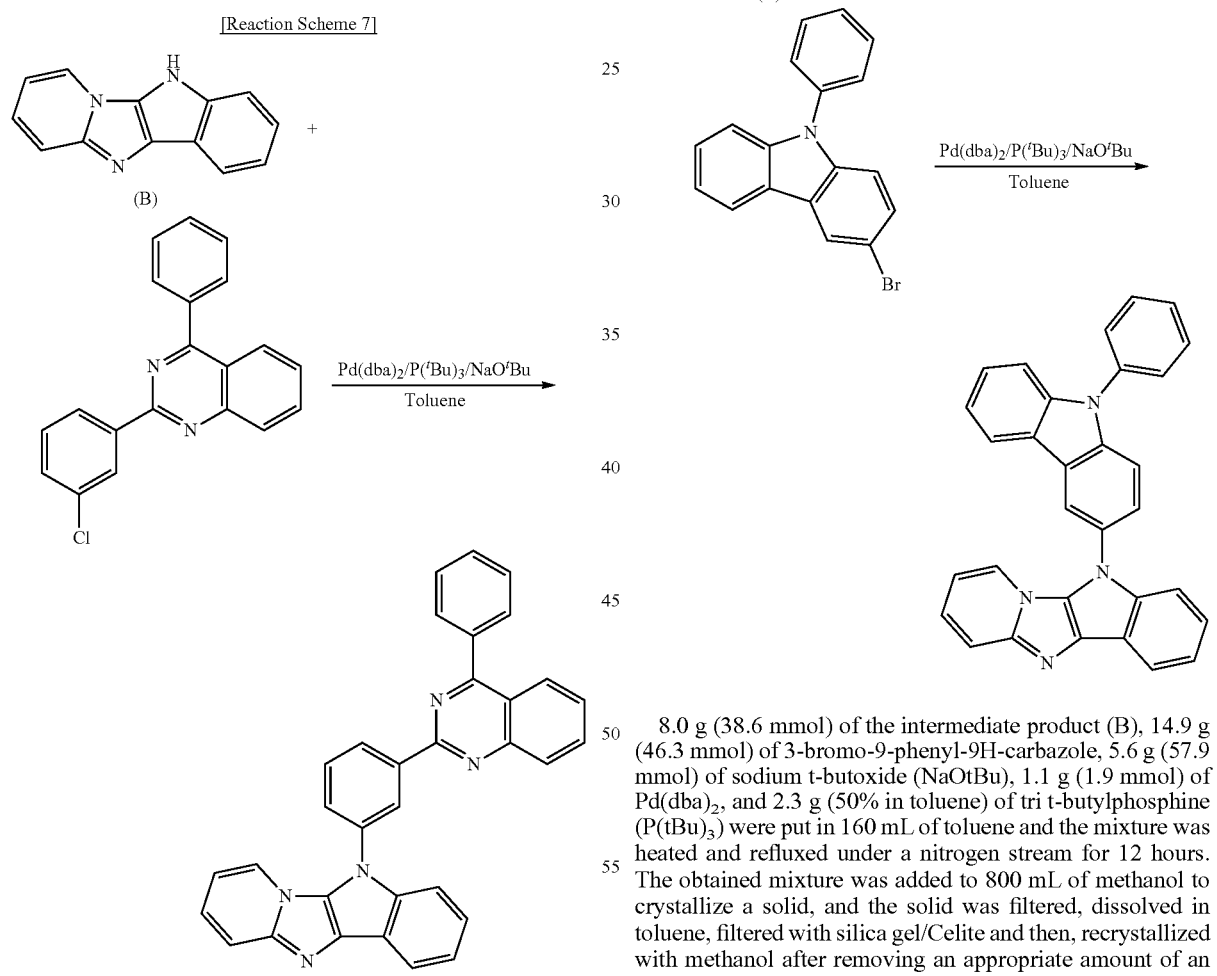

8.0 g (38.6 mmol) of the intermediate product (B), 14.7 g (46.3 mmol) of 2-(3-chloro-phenyl)-4-phenyl-quinazoline, 5.6 g (57.9 mmol) of sodium t-butoxide (NaOtBu), 1.1 g (1.9 mmol) of Pd(dba)$_2$, and 2.3 g (50% in toluene) of tri t-butylphosphine (P(tBu)$_3$) were put in 160 mL of toluene, and the mixture was heated and refluxed under a nitrogen stream for 12 hours. The obtained mixture was added to 1000 mL of methanol to crystallize a solid, and the solid was dissolved in toluene, filtered with silica gel/Celite and then, recrystallized after removing an appropriate amount of an organic solvent, obtaining 15.0 g (80%) of a compound A-43.

HRMS (70 eV, EI$^+$) m/z calcd for C33H21N5: 487.18. found for 487.53.

Example 8: Synthesis of Compound B-1

A compound B-1 as specific examples of a compound for an organic optoelectric device of the present invention was synthesized through the following Reaction Scheme.

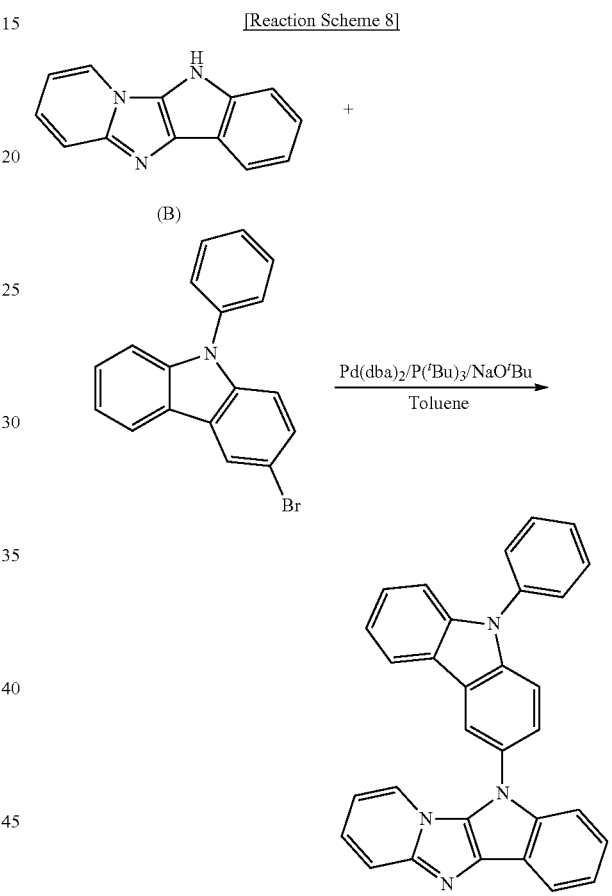

8.0 g (38.6 mmol) of the intermediate product (B), 14.9 g (46.3 mmol) of 3-bromo-9-phenyl-9H-carbazole, 5.6 g (57.9 mmol) of sodium t-butoxide (NaOtBu), 1.1 g (1.9 mmol) of Pd(dba)$_2$, and 2.3 g (50% in toluene) of tri t-butylphosphine (P(tBu)$_3$) were put in 160 mL of toluene and the mixture was heated and refluxed under a nitrogen stream for 12 hours. The obtained mixture was added to 800 mL of methanol to crystallize a solid, and the solid was filtered, dissolved in toluene, filtered with silica gel/Celite and then, recrystallized with methanol after removing an appropriate amount of an organic solvent, obtaining 12.0 g (69%) of a compound B-1.

HRMS (70 eV, EI$^+$) m/z calcd for C31H20N4: 448.17. found for 448.52.

Example 9: Synthesis of Compound B-4

A compound B4 as specific examples of a compound for an organic optoelectric device of the present invention was synthesized through the following Reaction Scheme.

[Reaction Scheme 9]

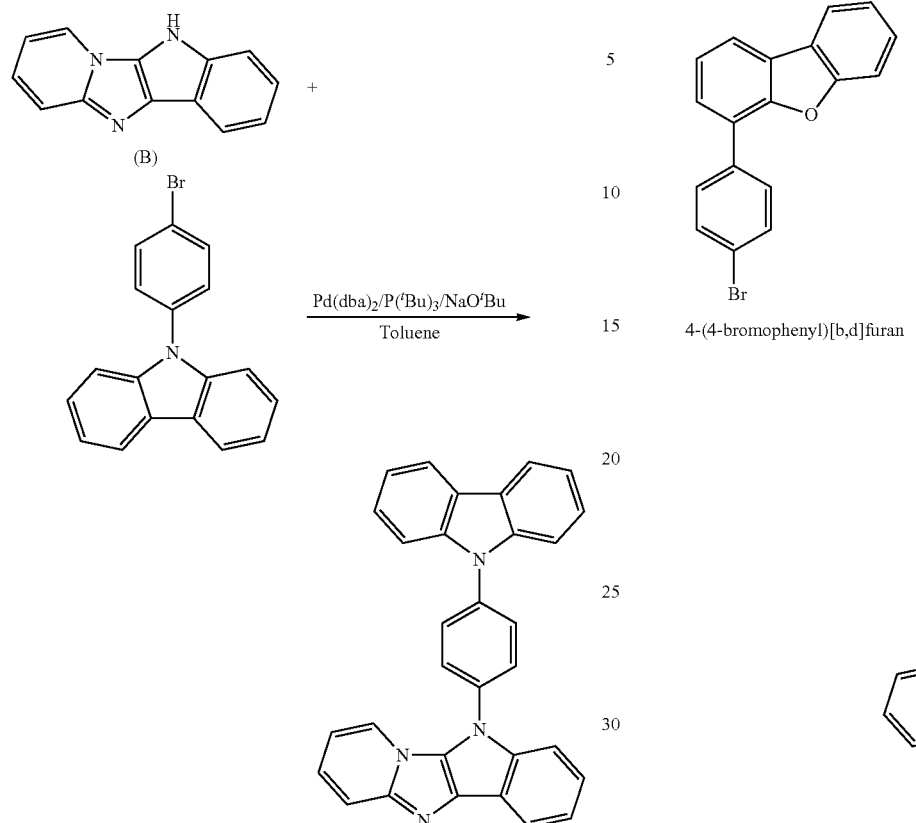

4-(4-bromophenyl)[b,d]furan 6.0 g (28.9 mmol) of the intermediate product (B), 11.2 g (34.7 mmol) of 9-(4-bromo-phenyl)-9H-carbazole, 4.2 g (43.4 mmol) of sodium t-butoxide (NaOtBu), 0.8 g (1.5 mmol) of Pd(dba)$_2$, and 1.8 g (50% in toluene) of tri t-butylphosphine (P(tBu)$_3$) were put in 120 mL of toluene, and the mixture was heated and refluxed under a nitrogen stream for 12 hours. The obtained mixture was added to 800 mL of methanol to crystallize a solid, dissolved in toluene, filtered with silica gel/Celite and then, recrystallized with methanol after removing an appropriate amount of an organic solvent, obtaining 8.0 g (62%) of a compound B-4.

HRMS (70 eV, EI$^+$) m/z calcd for C31H20N4: 448.17. found for 448.52.

Example 10: Synthesis of Compound B-11

A compound B11 as specific examples of a compound for an organic optoelectric device of the present invention was synthesized through the following Reaction Scheme.

6.0 g (28.9 mmol) of the intermediate product (B), 4-(4-bromo-phenyl)-dibenzofuran 11.2 g (34.7 mmol), sodium t-butoxide (NaOtBu) 4.2 g (43.4 mmol), Pd(dba)$_2$ 0.8 g (1.5 mmol), tri t-butylphosphine (P(tBu)$_3$) and 1.8 g (50% in toluene) were put in 120 mL of toluene, and the mixture was heated and refluxed under a nitrogen stream for 12 hours. The obtained mixture was added to 800 mL of methanol to crystallize a solid, and the solid was filtered, dissolved in toluene, filtered with silica gel/Celite and then, recrystallized with methanol after removing an appropriate amount of an organic solvent, obtaining 10.0 g (77%) of a compound B-11.

HRMS (70 eV, EI$^+$) m/z calcd for C31H19N3O: 449.15. found for 449.50.

Example 11: Synthesis of Compound B-13

A compound B13 as specific examples of a compound for an organic optoelectric device of the present invention was synthesized through the following Reaction Scheme.

[Reaction Scheme 10]

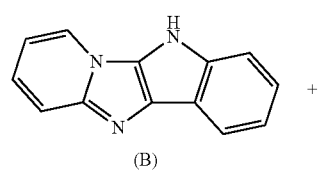

(B)

[Reaction Scheme 11]

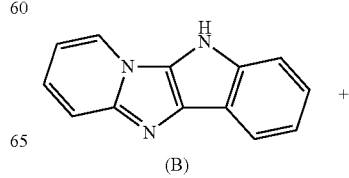

(B)

-continued

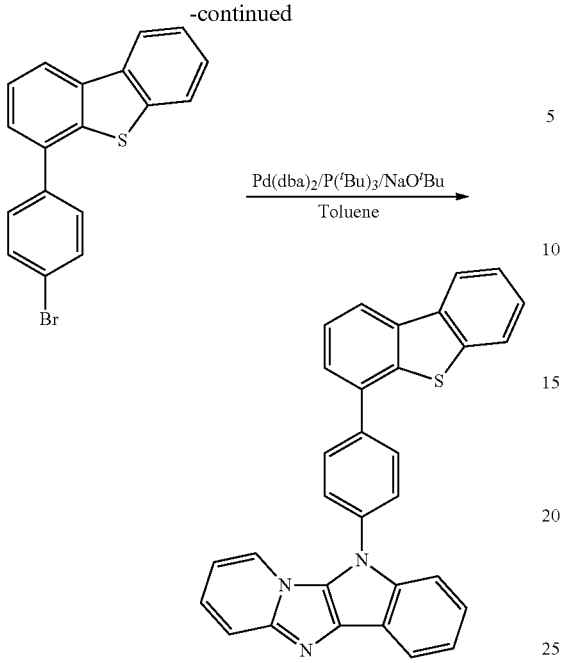

6.0 g (28.9 mmol) of the intermediate product (B), 11.8 g (34.7 mmol) of 4-(4-bromo-phenyl)-dibenzothiophene, 4.2 g (43.4 mmol) of sodium t-butoxide (NaOtBu), 0.8 g (1.5 mmol) of Pd(dba)$_2$, and 1.8 g (50% in toluene) of tri t-butylphosphine (P(tBu)$_3$) were put in 120 mL of toluene, and the mixture was heated and refluxed under a nitrogen stream for 12 hours. The obtained mixture was added to 800 mL of methanol to crystallize a solid, and the solid was filtered, dissolved in toluene, filtered with silica gel/Celite and then, recrystallized with methanol after removing an appropriate amount of an organic solvent, obtaining 12.0 g (89%) of a compound B-13.

HRMS (70 eV, EI$^+$) m/z calcd for C31H19N3S: 465.13. found for 465.48.

Comparative Examples 1 to 3

The following compounds were synthesized.
Comparative Examples 1, 2, and 3:

compound a

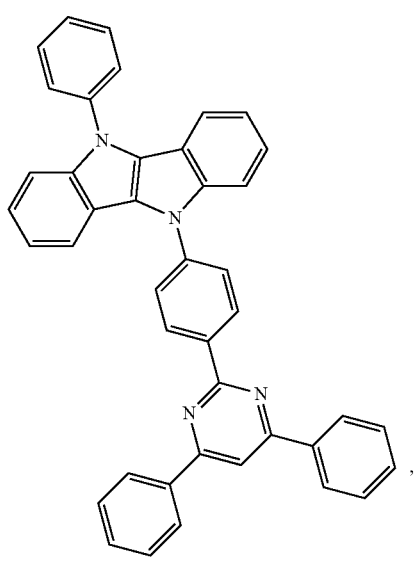

-continued compound b

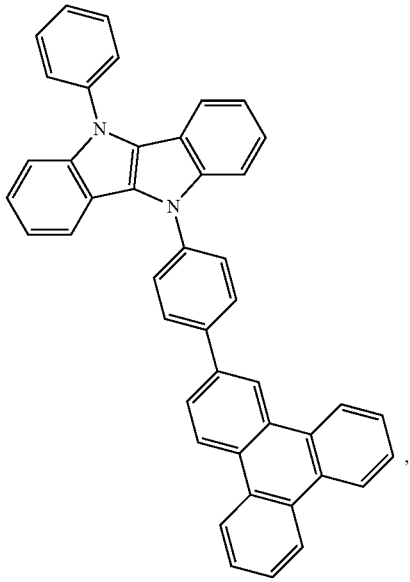

compound c

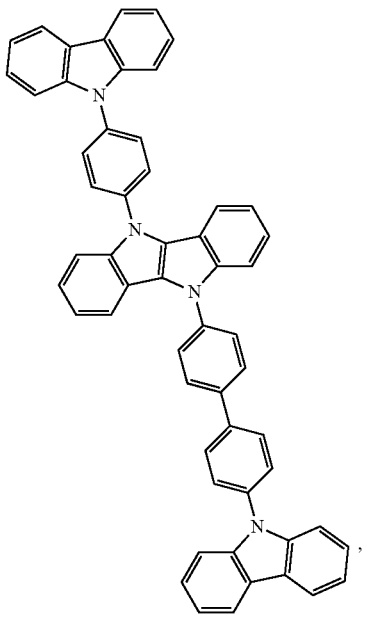

(Comparison of Simulation Characteristics of Compounds)

Energy level of each material was calculated in a Gaussian 09 method by using a super computer GAIA (IBM power 6), and the results are provided in the following Table 1.

TABLE 1

| | Simulation Data | | |
|---|---|---|---|
| Nos. | Compound | HOMO | LUMO |
| Example 1 | A-3 | −5.015 | −1.904 |
| Example 2 | A-5 | −5.21 | −2.066 |
| Example 3 | A-15 | −4.869 | −1.852 |
| Example 4 | A-17 | −4.966 | −2.093 |
| Example 5 | A-40 | −4.948 | −2.127 |
| Example 6 | A-41 | −4.939 | −2.168 |

TABLE 1-continued

| Nos. | Compound | HOMO | LUMO |
|---|---|---|---|
| Example 7 | A-43 | −4.818 | −2.148 |
| Comparative Example 1 | a | −4.786 | −1.708 |
| Comparative Example 2 | b | −4.821 | −1.297 |
| Comparative Example 3 | c | −4.989 | −1.024 |

Examples of the present invention has a lower LUMO energy level and easier electron injection from an electron transport layer (ETL) than Comparative Examples 1 to 3 and thus, may provide OLED having a low driving voltage and high luminous efficiency and life-span characteristics.

The compounds A-3 to A-17 may be not only applied to a green light emitting element as a single host but also mixed with the compounds B-1 to B-13 in various ratios. The compounds A-40 and A-41 may be applied to a red light emitting element as a single host.

Manufacture of Organic Light Emitting Diode

Example 12

An organic light emitting diode was manufactured by using the compound A-3 of Example 1 as a host and Ir(PPy)$_3$ as a dopant.

As for an anode, 1000 Å-thick ITO was used, and as for a cathode, 1000 Å-thick aluminum (Al) was used. Specifically, illustrating a method of manufacturing the organic light emitting diode, the anode is manufactured by cutting an ITO glass substrate having 15 Ω/cm$^2$ of sheet resistance into a size of 50 mm×50 mm×0.7 mm, ultrasonic wave-cleaning them in acetone, isopropylalcohol, and pure water for 15 minutes respectively, and UV ozone cleaning them for 30 minutes.

On the substrate, an 800 Å-thick hole transport layer (HTL) was formed by depositing N4,N4'-di(naphthalen-1-yl)-N4,N4'-diphenylbiphenyl-4,4'-diamine (NPB) under a vacuum degree 650×10-7 Pa at a deposition rate of 0.1 to 0.3 nm/s. Subsequently, A 300 Å-thick emission layer was formed by using the compound A-3 of Example 1 under the same vacuum deposition condition, and herein, a phosphorescent dopant of Ir(PPy)$_3$ was simultaneously deposited. Herein, the phosphorescent dopant was deposited to be 7 wt % based on 100 wt % of the entire weight of the emission layer by adjusting the deposition rate.

On the emission layer, a 50 Å-thick hole blocking layer was formed by depositing bis(2-methyl-8-quinolinolate)-4-(phenylphenolato)aluminium (BAlq) under the same vacuum deposition condition. Subsequently, a 200 Å-thick electron transport layer (ETL) was formed by depositing Alq3 under the same vacuum deposition condition. On the electron transport layer (ETL), a cathode is formed by sequentially depositing LiF and Al, manufacturing an organic optoelectric device.

The organic optoelectric device has a structure of ITO/NPB (80 nm) EML (compound A-3 (93 wt %)+Ir(PPy)$_3$ (7 wt %), 30 nm)/Balq (5 nm)/Alq3 (20 nm)/LiF (1 nm)/Al (100 nm).

Example 13

An organic light emitting diode was manufactured according to the same method as Example 12 except for using the compound A-5 instead of the compound A-3.

Example 14

An organic light emitting diode was manufactured according to the same method as Example 12 except for using the compound A-15 instead of the compound A-3.

Example 15

An organic light emitting diode was manufactured according to the same method as Example 12 except for using the compound A-17 instead of the compound A-3.

Example 16

An organic light emitting diode was manufactured according to the same method as Example 12 except for using the compounds A-5 and B-1 in a ratio of 1:1 instead of the compound A-3.

Example 17

An organic light emitting diode was manufactured according to the same method as Example 12 except for using the compounds A-5 and B-4 in a ratio of 1:1 instead of the compound A-3.

Example 18

An organic light emitting diode was manufactured according to the same method as Example 12 except for using the compounds A-17 and B-1 in a ratio of 1:1 instead of the compound A-3.

Example 19

An organic light emitting diode was manufactured according to the same method as Example 12 except for using the compounds A-17 and B-4 in a ratio of 1:1 instead of the compound A-3.

Comparative Example 4

An organic light emitting diode was manufactured according to the same method as Example 12 except for using CBP instead of the compound A-3.

The structures of the NPB, BAlq, CBP and Ir(PPy)$_3$ used to manufacture the organic light emitting diodes are as follows.

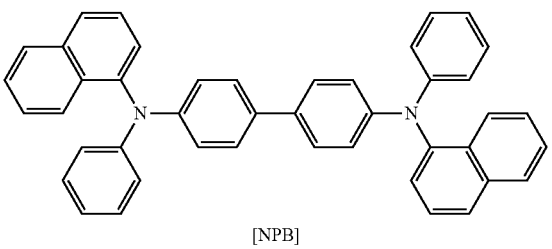

[NPB]

-continued

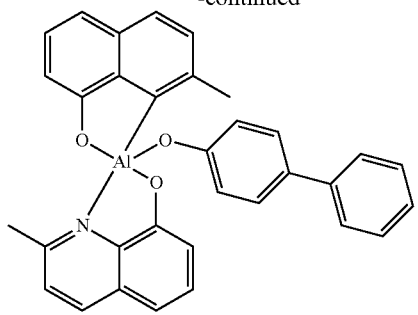

[BAlq]

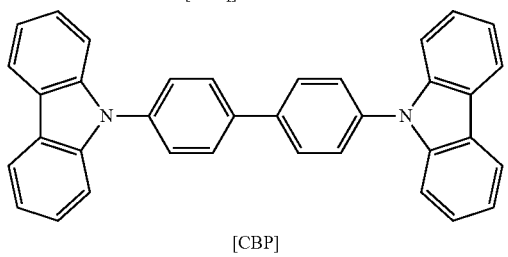

[CBP]

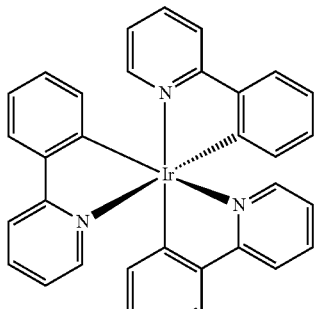

[Ir(PPy)₃]

Example 20

An organic light emitting diode was manufactured by using the compound A-40 of Example 5 as a host and (piq)₂Ir(acac) as a dopant.

As for an anode, 1000 Å-thick ITO was used, and as for a cathode, 1000 Å-thick aluminum (Al) was used. Specifically, illustrating a method of manufacturing the organic light emitting diode, the anode is obtained by cutting an ITO glass substrate having sheet resistance of 15 Ω/cm² into a size of 50 mm×50 mm×0.7 mm, ultrasonic wave cleaning them in acetone, isopropylalcohol, and pure water for 15 minutes respectively, and UV ozone cleaning them for 30 minutes.

On the substrate, an 800 Å-thick hole transport layer (HTL) was formed by depositing N4,N4'-di(naphthalen-1-yl)-N4,N4'-diphenylbiphenyl-4,4'-diamine (NPB) (80 nm) under a vacuum degree of 650×10-7 Pa at a deposition rate of 0.1 to 0.3 nm/s. Subsequently, a 300 Å-thick emission layer was formed by depositing the compound A-40 of Example 5 and simultaneously, a phosphorescent dopant of (piq)₂Ir(acac). Herein, the phosphorescent dopant was deposited in an amount of 3 wt % based on 100 wt % of the entire weight of the emission layer.

On the emission layer, a 50 Å-thick hole blocking layer was formed by depositing bis(2-methyl-8-quinolinolate)-4-(phenylphenolato)aluminium (BAlq) under the same vacuum deposition condition. Subsequently, a 200 Å-thick electron transport layer (ETL) was formed by depositing Alq3 under the same vacuum deposition condition. On the electron transport layer (ETL), a cathode is formed by sequentially depositing LiF and Al, manufacturing an organic optoelectric device.

The organic optoelectric device has a structure of ITO/NPB (80 nm)/EML (compound A-40 (97 wt %)+(piq)₂Ir(acac) (3 wt %), 30 nm)/Balq (5 nm)/Alq3 (20 nm)/LiF (1 nm)/Al (100 nm).

Example 21

An organic light emitting diode was manufactured according to the same method as Example 20 except for using the compound A-41 instead of the compound A-40.

Example 22

An organic light emitting diode was manufactured according to the same method as Example 20 except for using the compound A-43 instead of the compound A-40.

Comparative Example 5

An organic light emitting diode was manufactured according to the same method as Example 20 except for using CBP having the following structure instead of the compound A-40.

The structures of NPB, BAlq, CBP and (piq)₂Ir(acac) used to manufacture the organic light emitting diodes are as follows.

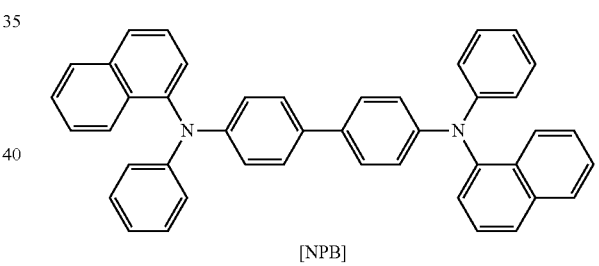

[NPB]

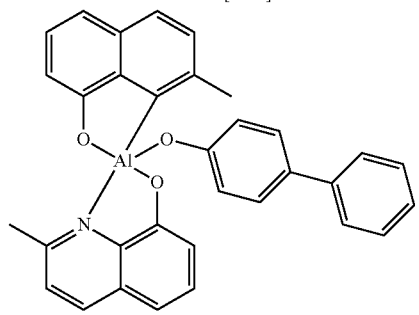

[BAlq]

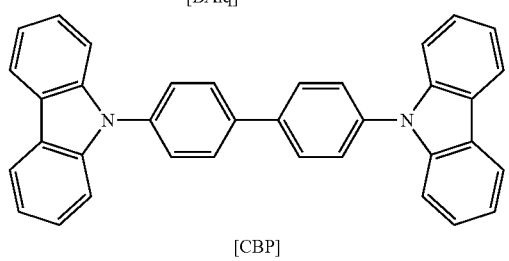

[CBP]

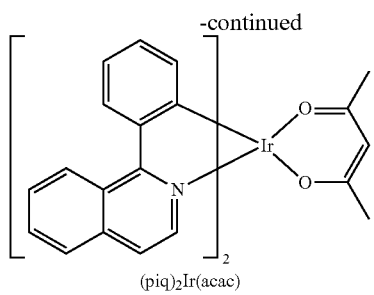

(piq)₂Ir(acac)

(Performance Evaluation of Organic Light Emitting Diode)

Current density and luminance changes depending on a voltage and luminous efficiency of each organic light emitting diode according to Examples 12 to 22 and Comparative Examples 4 and 5 were measured.

The measurements were specifically performed in the following method, and the results were provided in the following Table 2.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm²) were calculated by using the luminance, current density, and voltages (V) from the items (1) and (2).

(4) Measurement of Life-Span

Life-span was obtained by measuring time taken until current efficiency (cd/A) decreased down to 90% while luminance (cd/m²) was maintained at 5000 cd/m².

TABLE 2

| No. | Compound | Driving voltage (V) | Color (EL color) | Efficiency (cd/A) | 90% life-span (h) at 5000 cd/m² |
|---|---|---|---|---|---|
| Example 12 | compound A-3 | 3.8 | Green | 60.2 | 200 |
| Example 13 | compound A-5 | 4.2 | Green | 58.4 | 150 |
| Example 14 | compound A-15 | 4.0 | Green | 65.3 | 180 |
| Example 15 | compound A-17 | 4.1 | Green | 62.8 | 170 |
| Comparative Example 4 | CBP | 4.8 | Green | 31.4 | 40 |

TABLE 3

| | First host | Second host | Driving voltage (V) | Efficiency (cd/A) | 90% life-span (h) at 5000 cd/m² |
|---|---|---|---|---|---|
| Example16 | compound A-5 | compound B-1 | 3.8 | 62.3 | 200 |
| Example17 | compound A-5 | compound B-4 | 4.0 | 58.1 | 180 |
| Example18 | compound A-17 | compound B-1 | 3.9 | 61.6 | 190 |
| Example19 | compound A-17 | compound B-4 | 4.0 | 55.4 | 180 |
| Comparative Example 4 | | CBP | 4.8 | 31.4 | 40 |

TABLE 4

| No. | Compound | Driving voltage (V) | Color (EL color) | Efficiency (cd/A) | 90% life-span (h) at 5000 cd/m² |
|---|---|---|---|---|---|
| Example 20 | compound A-40 | 4.8 | Red | 11.1 | 100 |
| Example 21 | compound A-41 | 4.6 | Red | 13.4 | 150 |
| Example 22 | compound A-43 | 4.5 | Red | 10.1 | 130 |
| Comparative Example 5 | CBP | 6.5 | Red | 5.8 | 20 |

Referring to Table 2, the green organic light emitting diodes according to Examples 12 to 15 showed remarkably improved luminous efficiency and life-span compared with the organic light emitting diode according to Comparative Example 4.

Specifically, the compound for the organic light emitting diodes according to Examples 12 to 15 as a single host having a bipolar structure had an energy level capable of easily transporting electrons and holes and thus, realized a lower driving voltage and higher luminous efficiency and life-span characteristics than the organic light emitting diode according to Comparative Example 4.

Referring to Table 3, the organic light emitting diodes according to Examples 16 to 19 had an appropriate balance between hole and electron flows by using a first host having high electron characteristics and a second host having high hole characteristics and thus, showed higher efficiency and life-span characteristics than the organic light emitting diode according to Comparative Example 4.

In addition, referring to Table 4, the compound used in the red organic light emitting diodes according to Examples 20 to 22 was a single bipolar host having excellent hole and electron characteristics and had an appropriate energy level for a red light emitting element and thus, increased efficiency and life-span characteristics compared with the red light emitting element according to Comparative Example 5.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS 100, 200: organic light emitting diode
110: cathode
120: anode
105: organic layer
130, 230: emission layer
140: hole auxiliary layer

What is claimed is:

1. A compound for an organic optoelectric device represented by the following Chemical Formula I:

[Chemical Formula I]

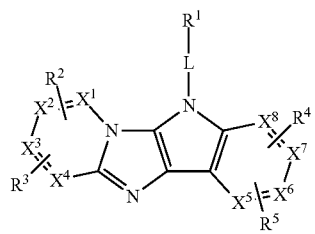

wherein, in the Chemical Formula I, $X^1$ to $X^8$ are independently N, C or $CR^a$, L is a single bond, a substituted or unsubstituted C6 to C30 arylene group, or a substituted or unsubstituted C2 to C30 heteroarylene group, $R^1$ is a substituted or unsubstituted C6 to C30 aryl group, a substituted or unsubstituted C2 to C30 heteroaryl group, or a combination thereof, $R^2$ to $R^5$ and $R^a$ are independently hydrogen, deuterium, a substituted or unsubstituted C6 to C30 aryl group, or a substituted or unsubstituted C2 to C30 heteroaryl group, and the $R^2$ and $R^3$, or $R^4$ and $R^5$ are independently present, or are fused to each other to provide a ring.

2. The compound for an organic optoelectric device of claim 1, wherein the Chemical Formula I is represented by one of the following Chemical Formulae 1 to 4:

[Chemical Formula 1]

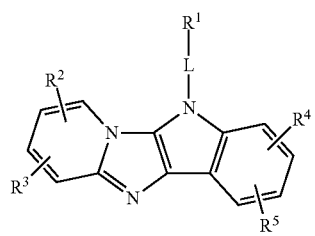

[Chemical Formula 2]

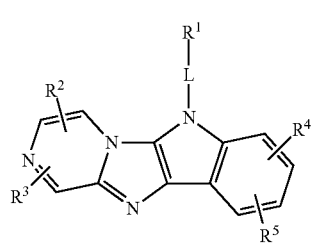

[Chemical Formula 3]

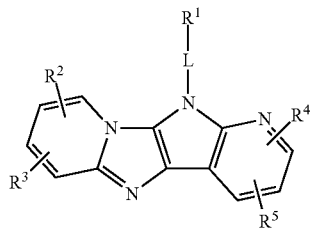

[Chemical Formula 4]

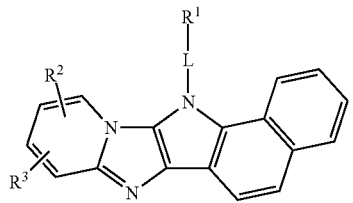

wherein, in the Chemical Formulae 1 to 4,

L is a single bond, a substituted or unsubstituted C6 to C30 arylene group, or a substituted or unsubstituted C2 to C30 heteroarylene group, $R^1$ is a substituted or unsubstituted C6 to C30 aryl group, a substituted or unsubstituted C2 to C30 heteroaryl group, or a combination thereof, and $R^2$ to $R^5$ are independently hydrogen, deuterium, a substituted or unsubstituted C6 to C30 aryl group, or a substituted or unsubstituted C2 to C30 heteroaryl group.

3. The compound for an organic optoelectric device of claim 1, wherein the Chemical Formula I is represented by one of the following Chemical Formulae 5 to 8:

[Chemical Formula 5]

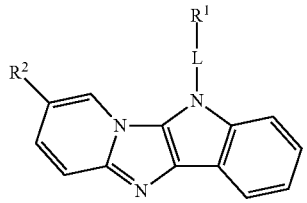

[Chemical Formula 6]

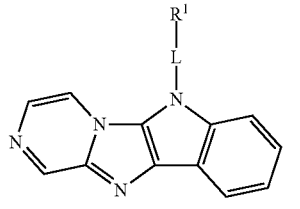

[Chemical Formula 7]

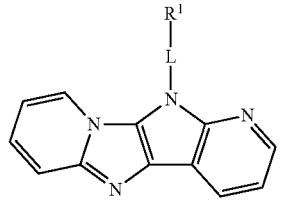

-continued

[Chemical Formula 8]

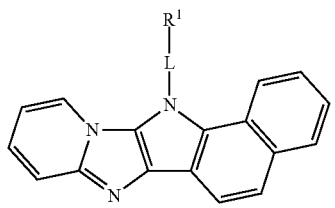

wherein, in the Chemical Formulae 5 to 8,

L is a single bond, a substituted or unsubstituted C6 to C30 arylene group, or a substituted or unsubstituted C2 to C30 heteroarylene group, $R^1$ is a substituted or unsubstituted C6 to C30 aryl group, a substituted or unsubstituted C2 to C30 heteroaryl group, or a combination thereof, and $R^2$ is hydrogen, deuterium, a substituted or unsubstituted C6 to C30 aryl group, or a substituted or unsubstituted C2 to C30 heteroaryl group.

4. The compound for an organic optoelectric device of claim 1, wherein the $R^1$ is a heteroaryl-containing moiety selected from moieties in the following Group I:

[Group I]

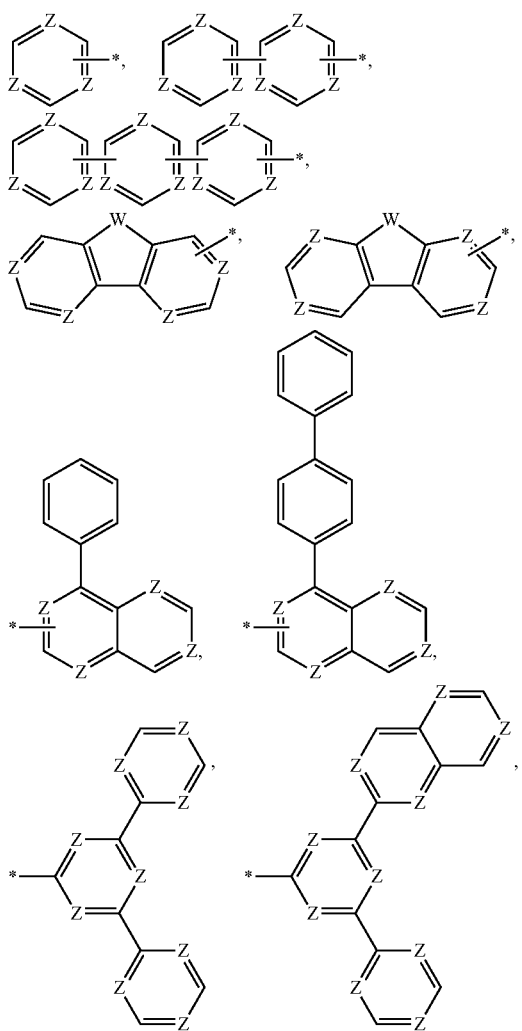

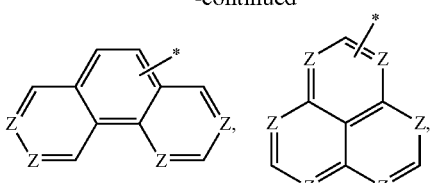

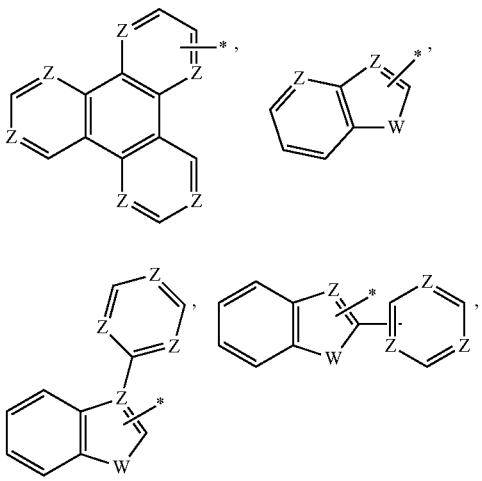

wherein, in the Group I,

Z are independently N or $CR^b$, at least one of Z is N,

W is $NR^c$, O, S, SO, $SO_2$, $CR^dR^e$, or $SiR^fR^g$, wherein $R^b$ to $R^g$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and \* is a linking point and may be positioned at one of element consisting of the functional groups.

5. The compound for an organic optoelectric device of claim 4, wherein the moieties listed in the Group I is represented by one of moieties listed in the following Group I-1:

[Group I-1]

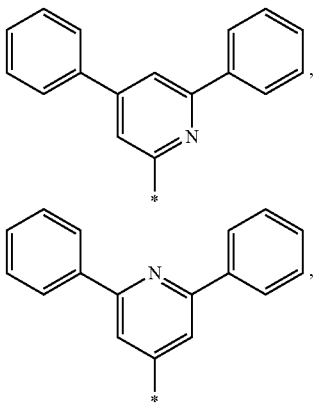

-continued

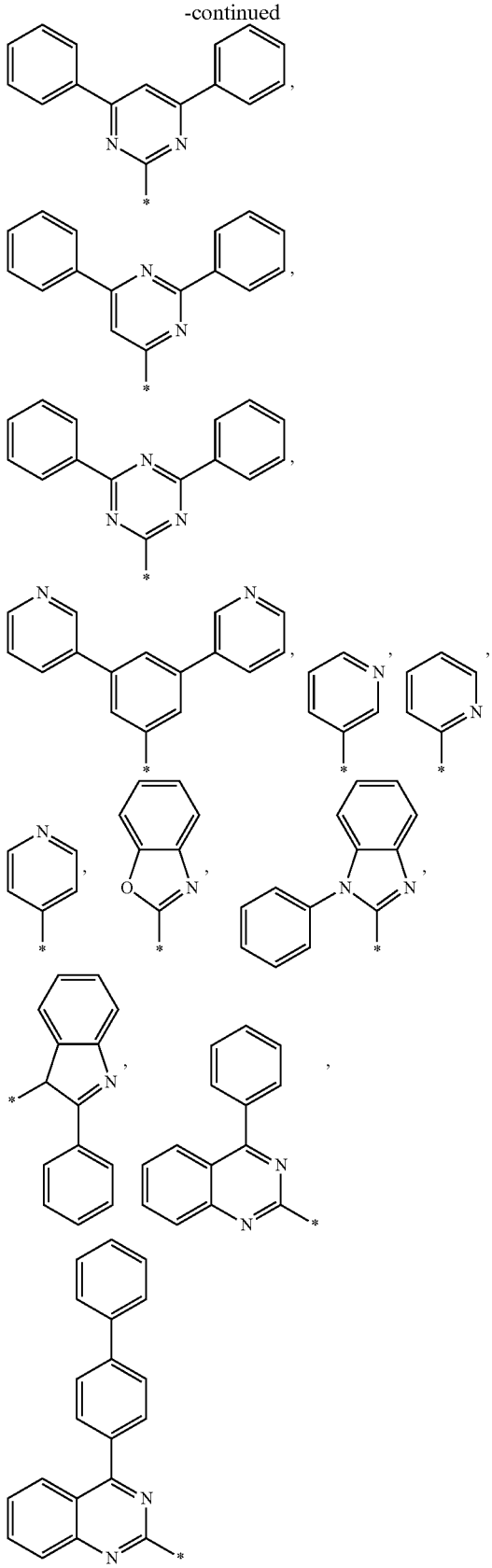

wherein, in the Group I-1,
* is a linking point.

6. The compound for an organic optoelectric device of claim 1, wherein the $R^1$ is selected from moieties in the following Group II:

[Group II]

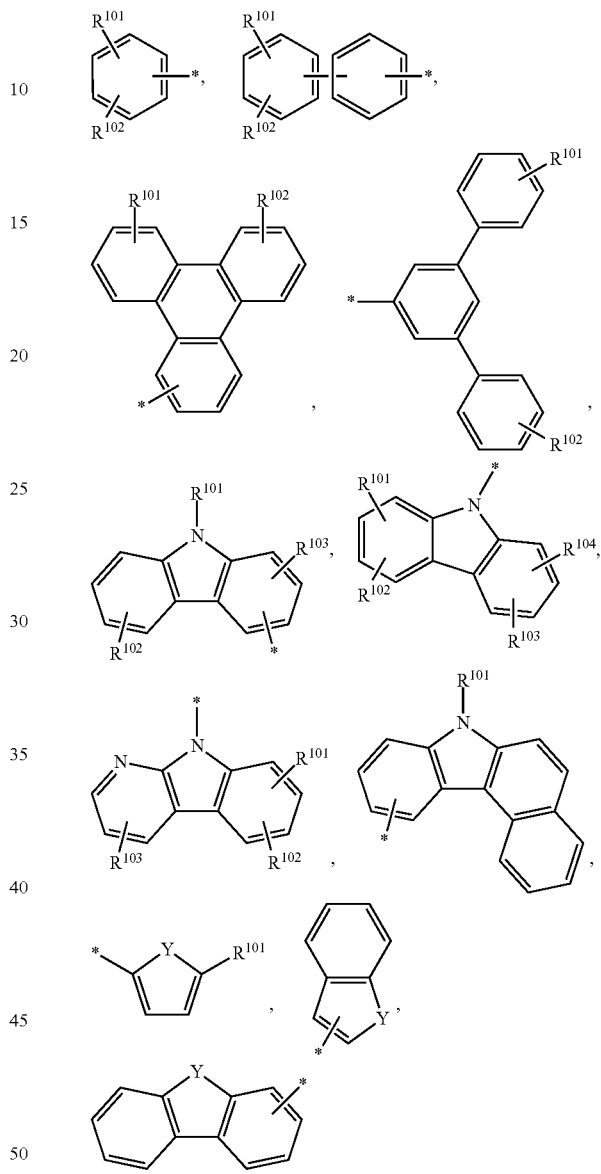

wherein, in the Group II, $R^{101}$ to $R^{104}$ are independently hydrogen, deuterium, a substituted or unsubstituted C1 to C30 alkyl group, a substituted or unsubstituted C1 to C30 silyl group, a substituted or unsubstituted C6 to C30 aryl group, or a combination thereof, Y is O, S, SO, or $SO_2$, and

* is a linking point and may be positioned at one of element consisting of the functional groups.

7. The compound for an organic optoelectric device of claim 6, wherein the moieties listed in the Group II are represented by one of moieties listed in the following Group II-1:

[Group II-1]

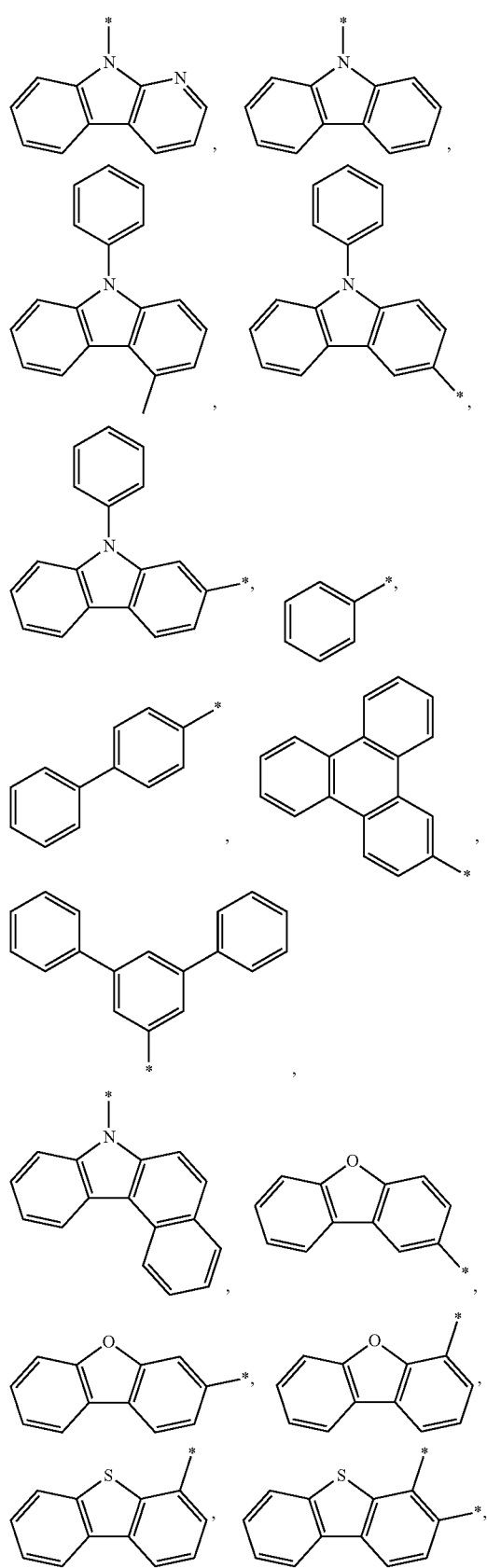

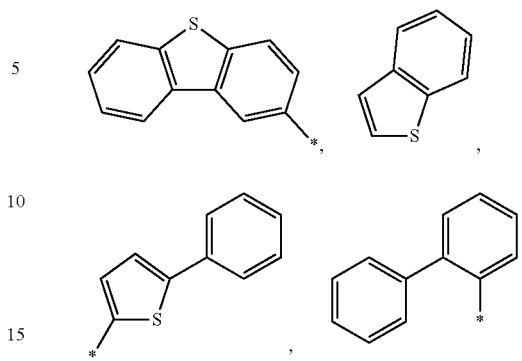

wherein, in the Group II-1,

* is a linking point.

8. The compound for an organic optoelectric device of claim 1, wherein the substituted or unsubstituted C6 to C30 arylene group, or a substituted or unsubstituted C2 to C30 heteroarylene group is a substituted or unsubstituted phenylene group, a substituted or unsubstituted biphenylene group, a substituted or unsubstituted terphenylene group, a substituted or unsubstituted pyridylene group, or a combination thereof.

9. The compound for an organic optoelectric device of claim 8, wherein the substituted or unsubstituted phenylene group, or the substituted or unsubstituted pyridylene group are one of moieties of the following Group III:

[Group III]

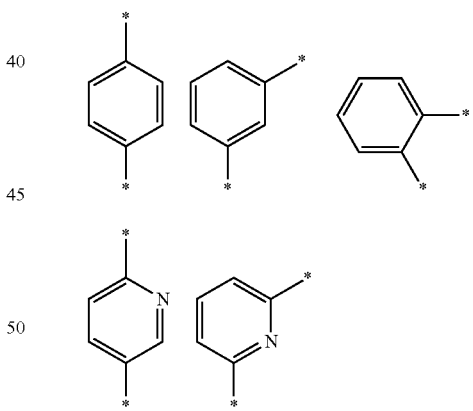

wherein, in the Group III,

* is a linking point.

10. The composition for an organic optoelectric device comprising
the first compound for an organic optoelectric device of claim 4 and a second compound for an organic optoelectric device of claim 6.

11. The composition for an organic optoelectric device of claim 10, wherein the first compound for an organic optoelectric device is selected from compounds listed in the following Group I-2:

[Group I-2]
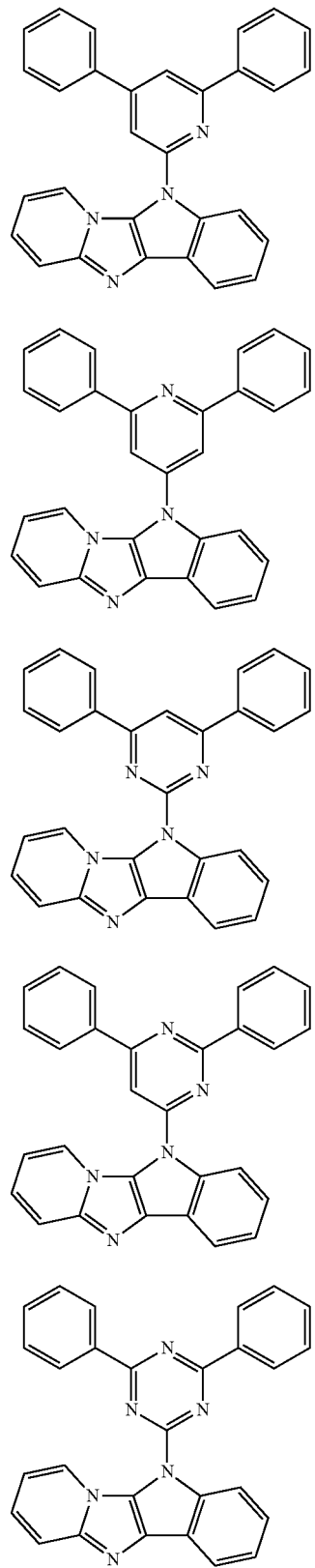
A-1
A-2
A-3
A-4
A-5
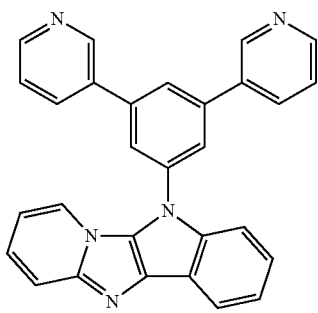
A-6
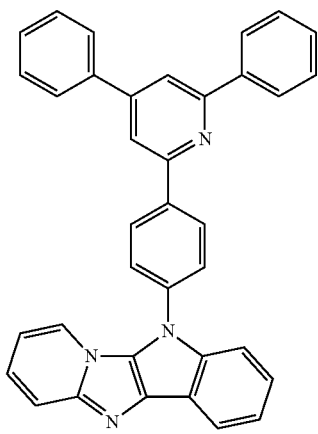
A-7
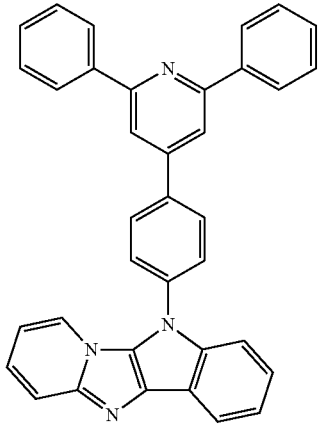
A-8
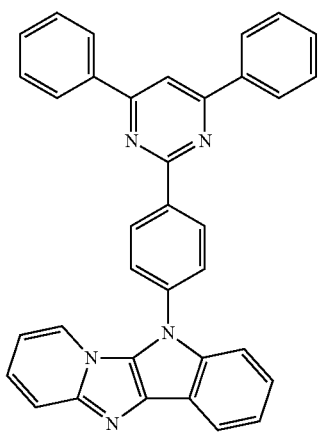
A-9

A-10
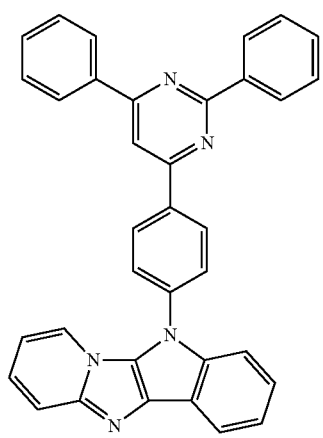
A-11
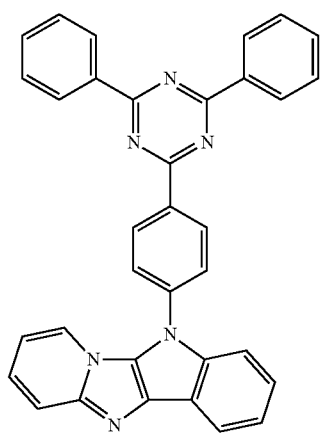
A-12
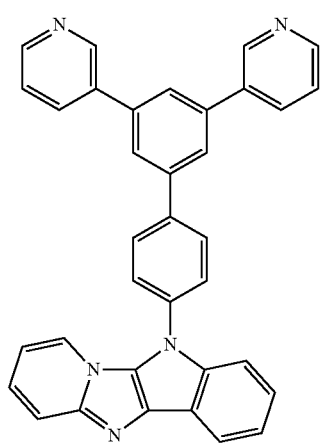
A-13
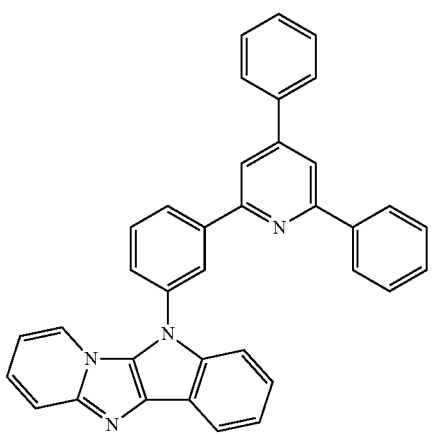
A-14
A-15
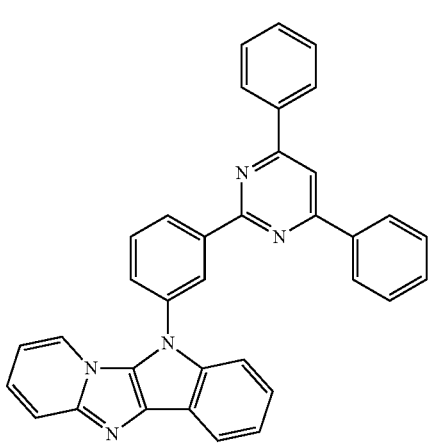

A-16
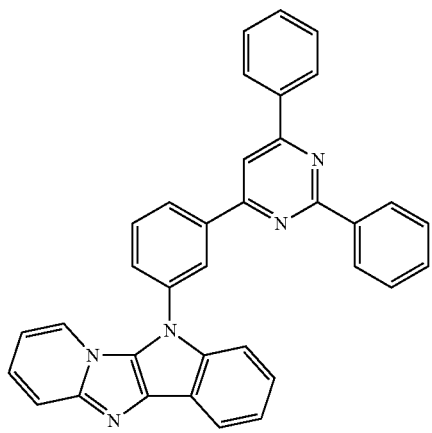
A-17
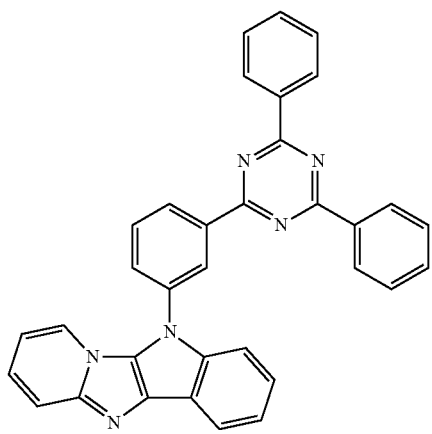
A-18
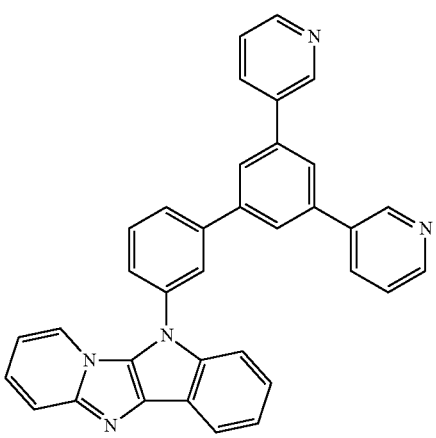
A-19
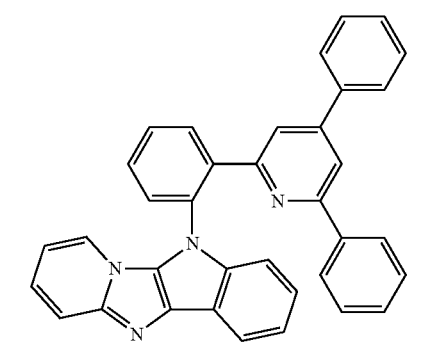
A-20
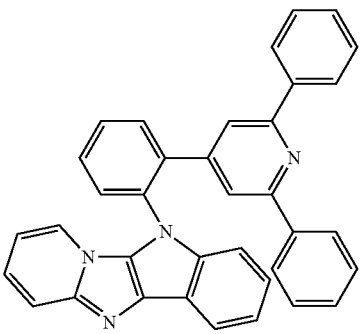
A-21
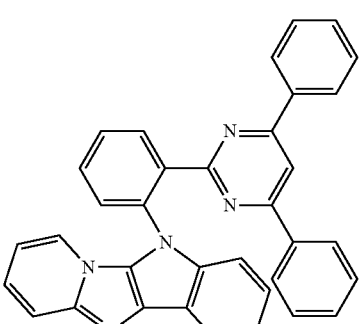
A-22
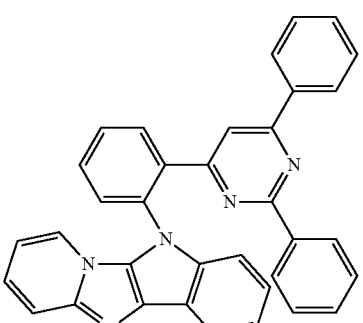
A-23
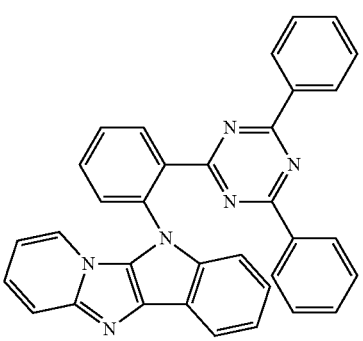

A-24
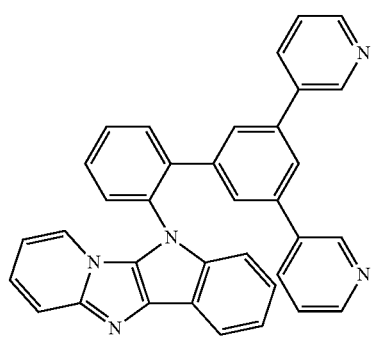
A-35
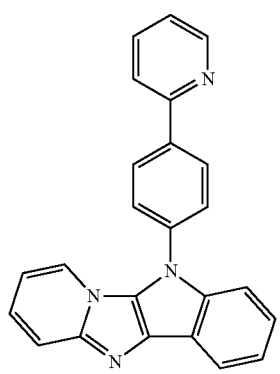
A-26
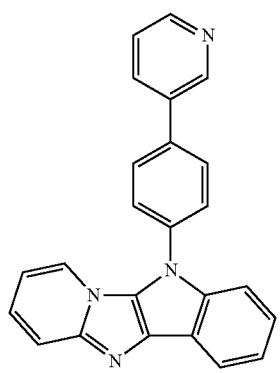
A-27
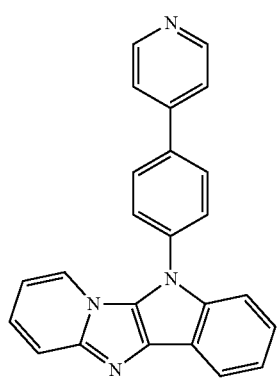
A-28
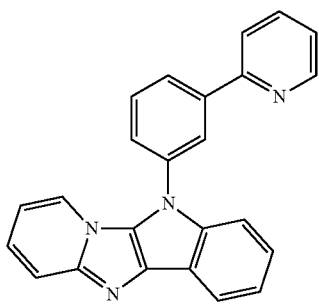
A-29
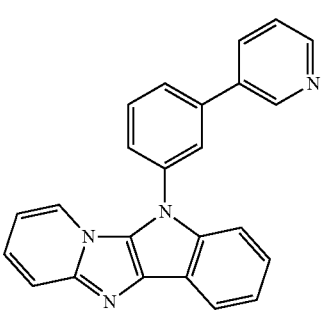
A-30
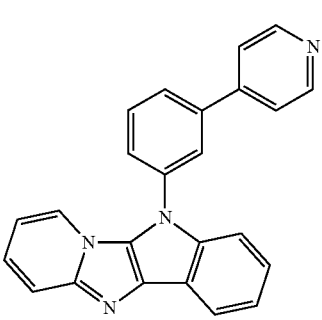
A-31
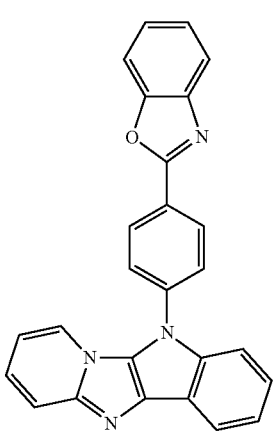

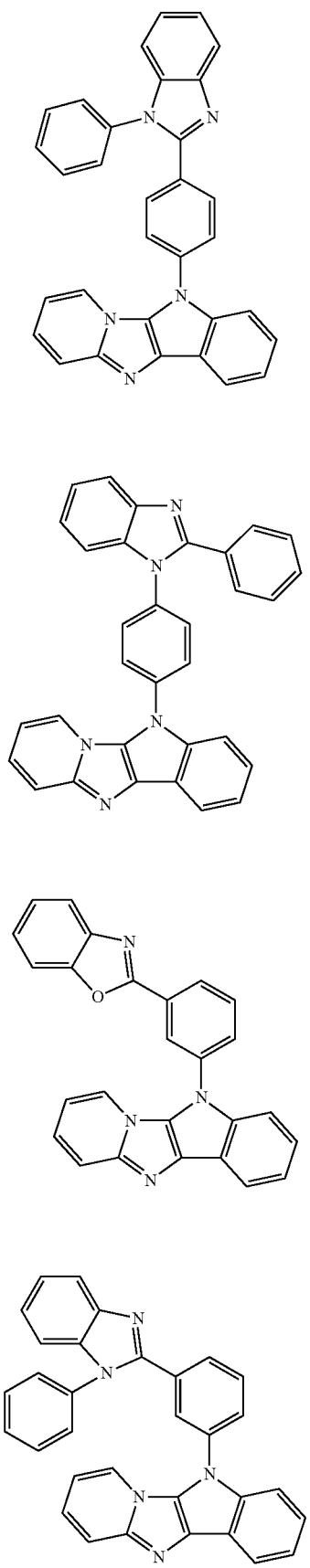
A-32
A-33
A-34
A-35
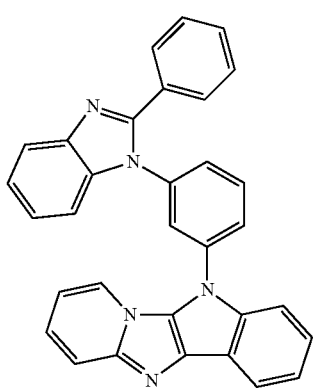
A-36
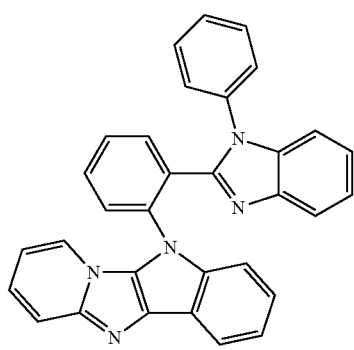
A-37
A-38
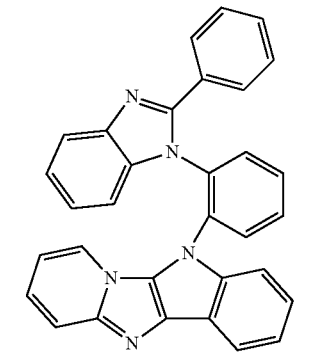
A-39
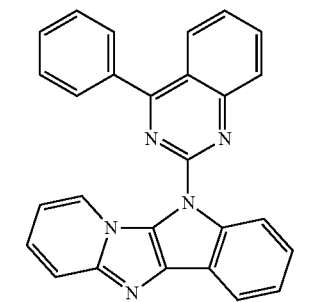
A-40

-continued
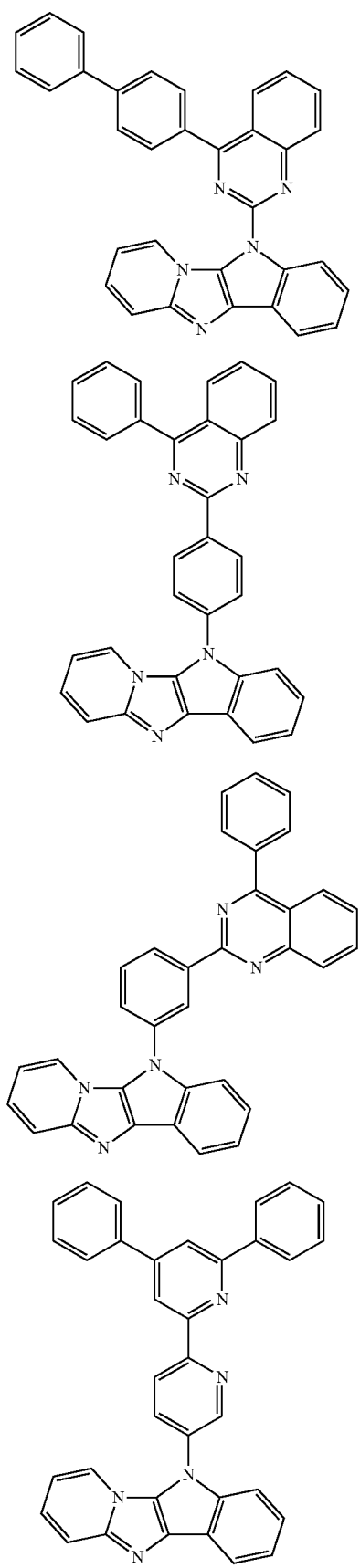
A-41
A-42
A-43
A-44
-continued
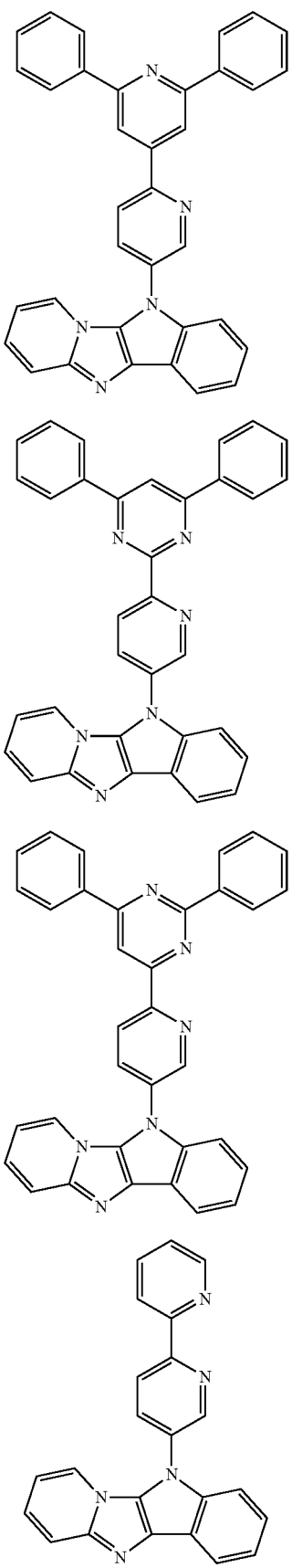
A-45
A-46
A-47
A-48

A-49
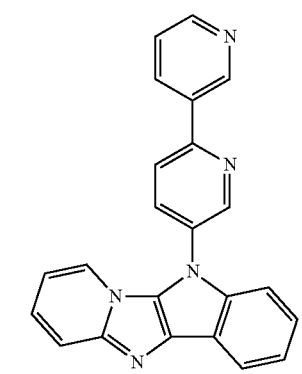
A-50
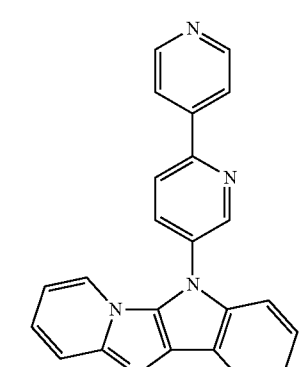
A-51
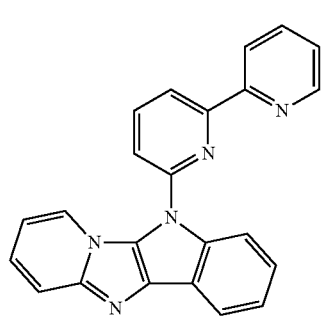
A-52
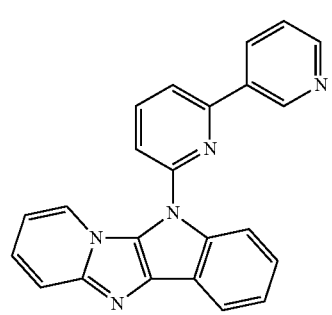
A-53
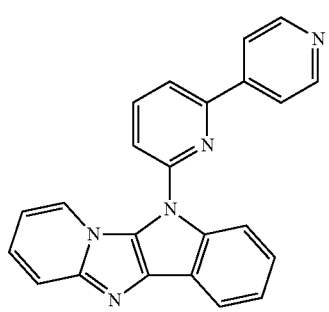
A-54
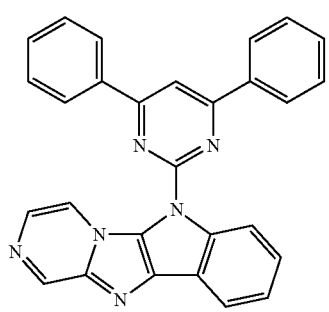
A-55
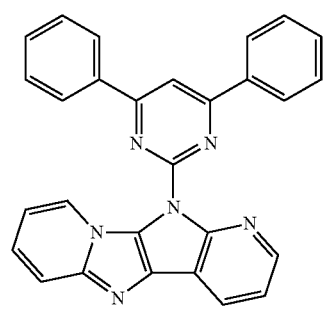
A-56
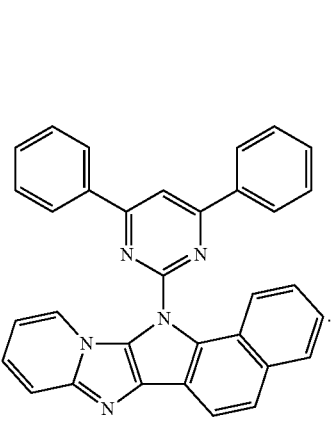
12. The composition for an organic optoelectric device of claim 10, wherein the second compound for an organic optoelectric device is selected from compounds listed in the following Group II-2:

[Group II-2]
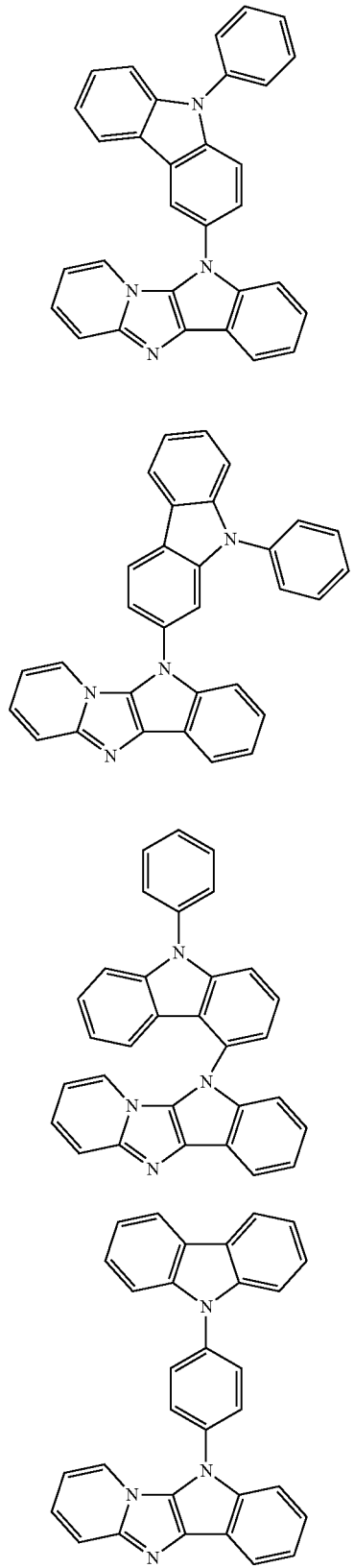
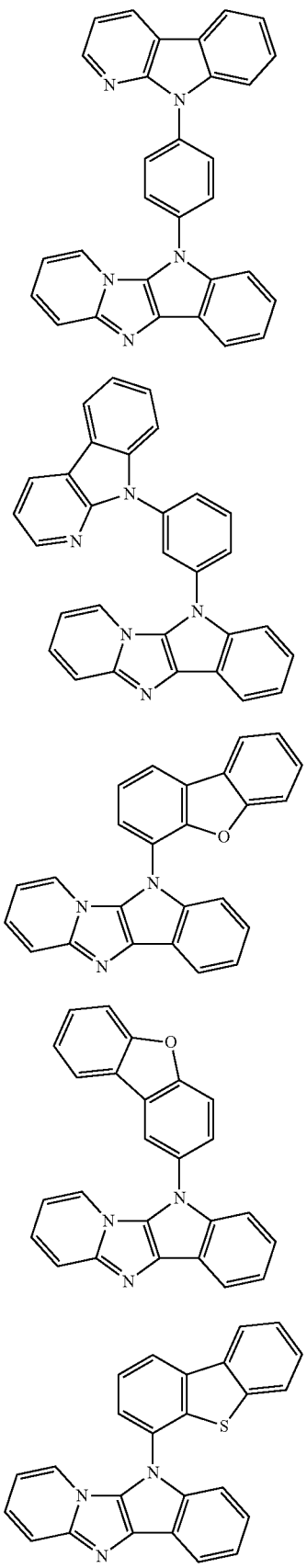

-continued
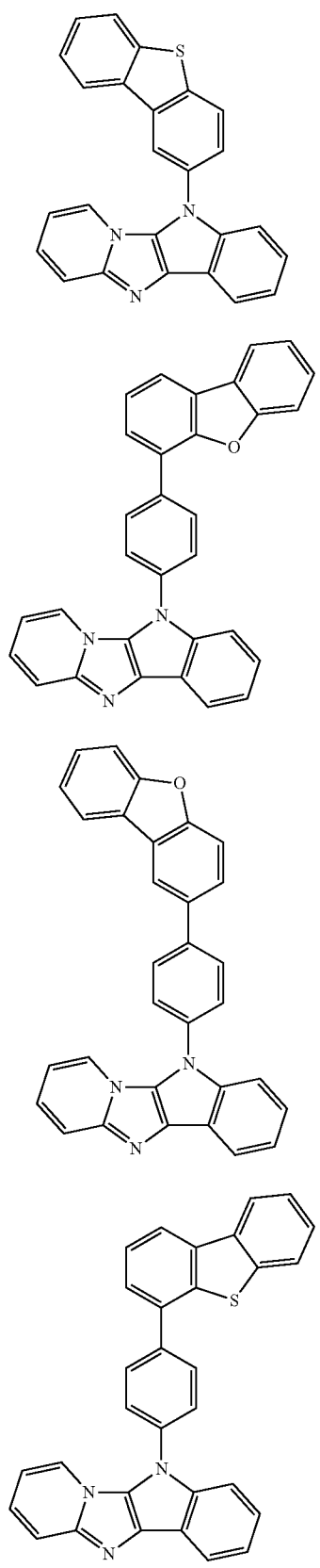
B-10
B-11
B-12
B-13
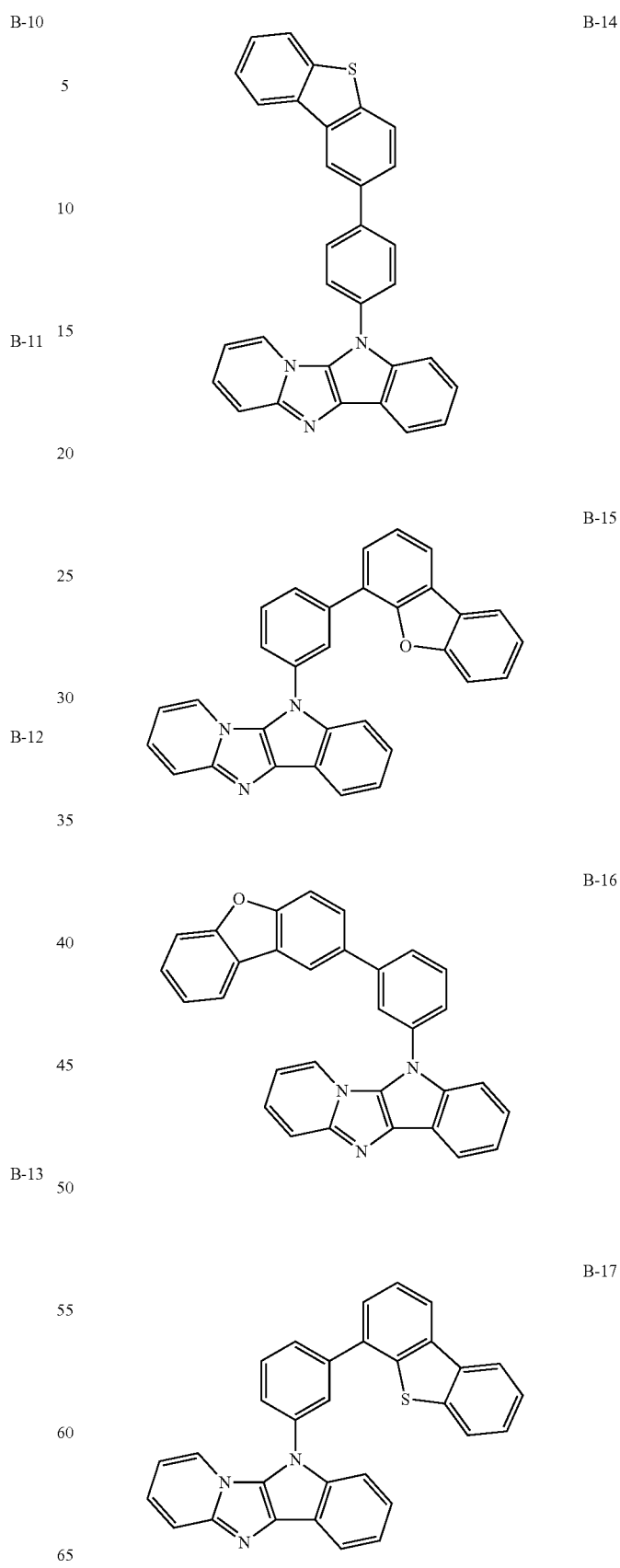
B-14
B-15
B-16
B-17

B-18
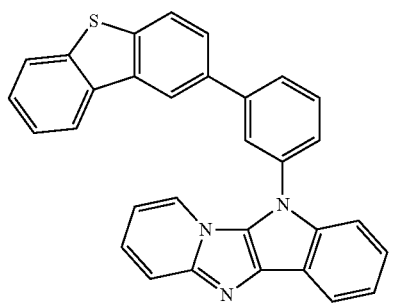
B-19
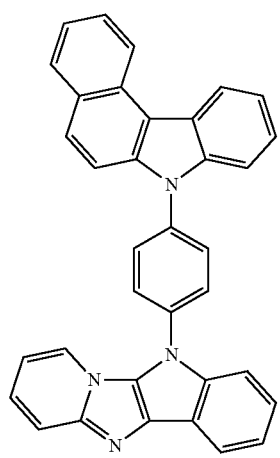
B-20
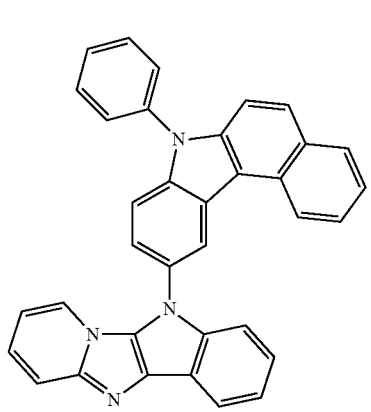
B-21
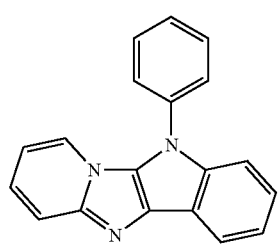
B-22
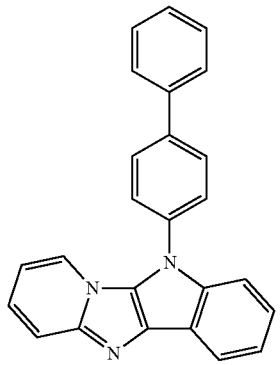
B-23
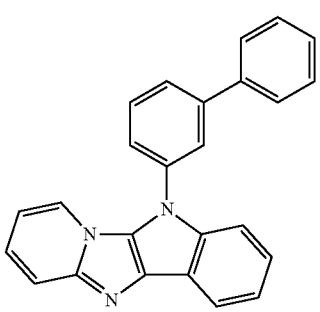
B-24
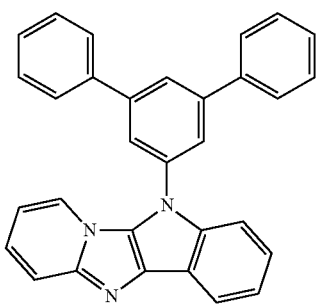
B-25
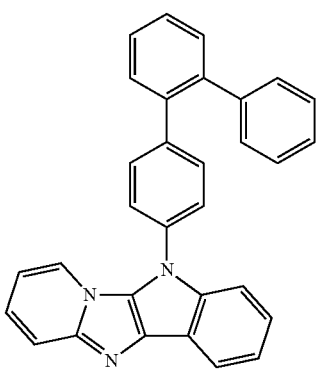

B-26
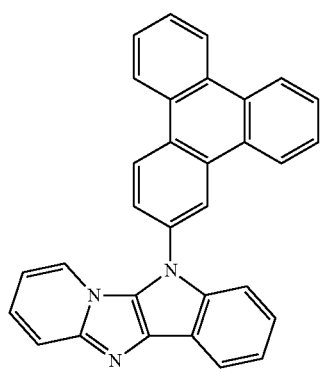
B-27
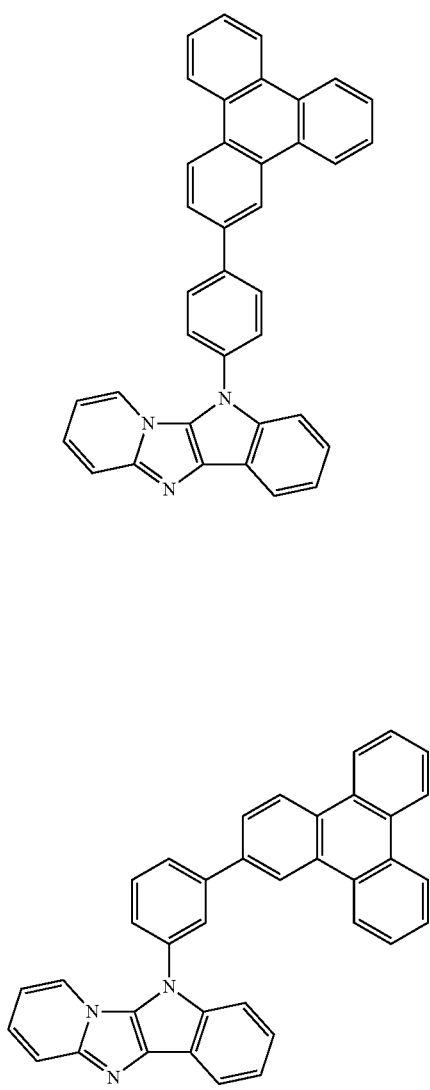
B-29
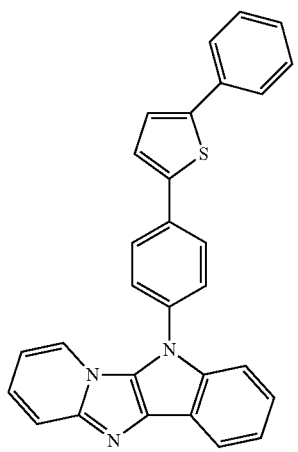
B-30
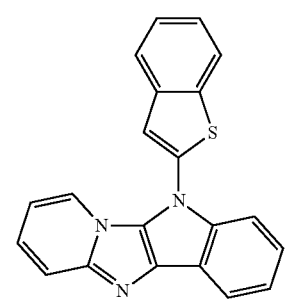
B-31
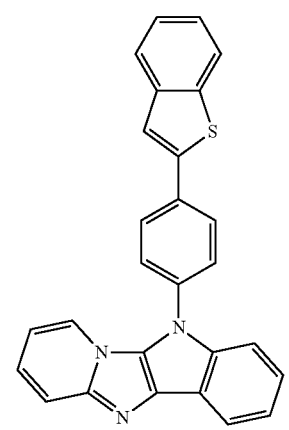
B-32
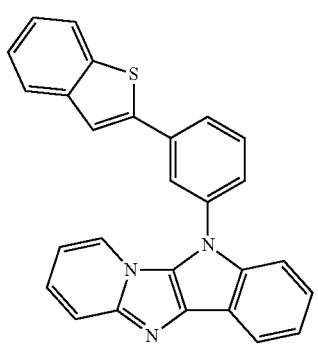
B-28

B-33
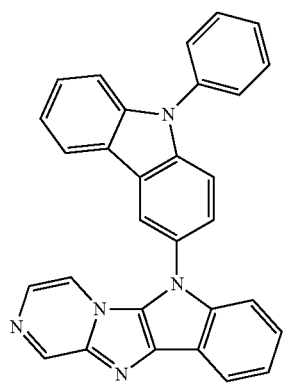
B-34
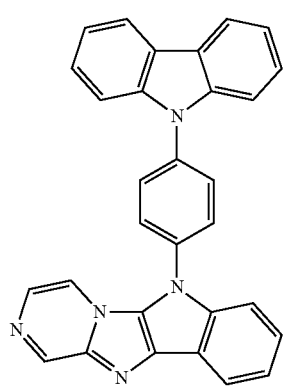
B-35
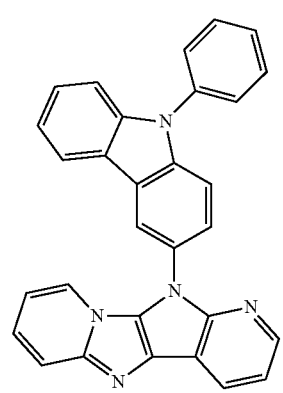
B-36
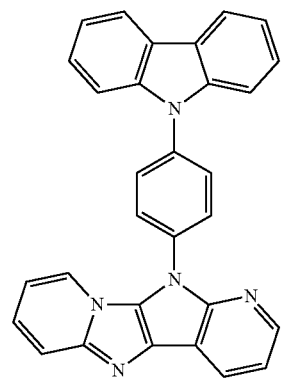
B-37
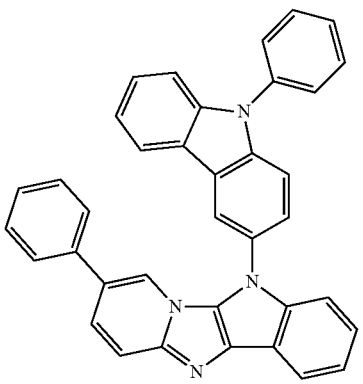
B-38
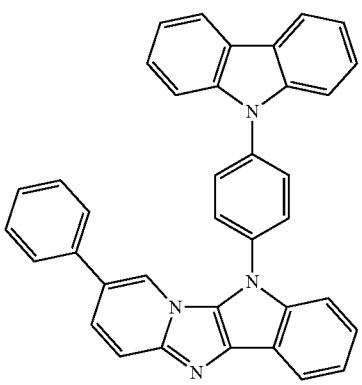
B-39
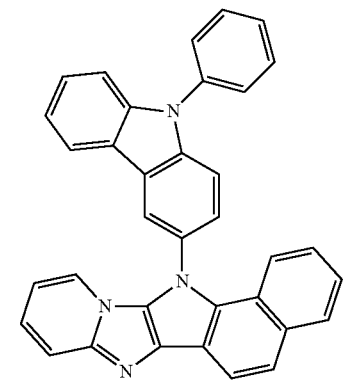
B-40
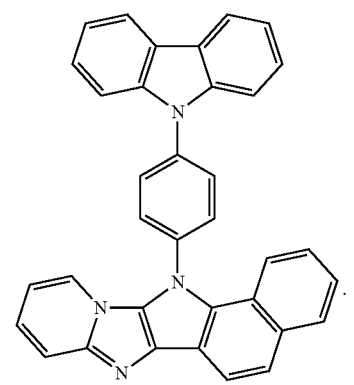
13. The composition for an organic optoelectric device of claim 10, wherein the first compound for an organic optoelectric device and the second compound for an organic optoelectric device are included in a weight ratio of about 1:10 to about 10:1.

14. The composition for an organic optoelectric device of claim 10, wherein the first compound for an organic optoelectric device and the second compound for an organic optoelectric device are used as a first host compound and a second host compound, respectively and
comprises a dopant.

15. An organic optoelectric device comprising
an anode and a cathode facing each other, and
at least one organic layer interposed between the anode and the cathode,
wherein the organic layer comprises the compound for an organic optoelectric device of claim 1 or the composition for an organic optoelectric device of claim 10.

16. The organic optoelectric device of claim 15, wherein the organic layer comprises an emission layer,
the emission layer comprises the compound for an organic photoelectric device or the composition for an organic optoelectric device.

17. The organic optoelectric device of claim 15, wherein the organic layer comprises at least one auxiliary layer selected from a hole injection layer, a hole transport layer, an electron blocking layer, an electron transport layer, an electron injection layer, and a hole blocking layer, and
the auxiliary layer comprises the compound for an organic optoelectric device or the composition for an organic optoelectric device.

18. The organic optoelectric device of claim 16, wherein the compound for an organic optoelectric device or the composition for an organic optoelectric device are included as a host of the emission layer.

19. A display device comprising the organic optoelectric device of claim 15.

* * * * *